(12) United States Patent
Liu et al.

(10) Patent No.: US 11,492,637 B2
(45) Date of Patent: Nov. 8, 2022

(54) RESISTANCE GENES ASSOCIATED WITH DISEASE RESISTANCE IN SOYBEANS

(71) Applicant: Syngenta Participations AG, Basel (CH)

(72) Inventors: Qingli Liu, Research Triangle Park, NC (US); Andrew David Farmer, Sante Fe, NM (US); Xiaoping Tan, Research Triangle Park, NC (US); Thomas Joseph Curley, Jr., Research Triangle Park, NC (US); Becky Welsh Breitinger, Research Triangle Park, NC (US); John Luther Dawson, Research Triangle Park, NC (US); John Daniel Hipskind, Research Triangle Park, NC (US); Robert Arthur Dietrich, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 19 days.

(21) Appl. No.: 16/765,717

(22) PCT Filed: Nov. 16, 2018

(86) PCT No.: PCT/US2018/061411
§ 371 (c)(1),
(2) Date: May 20, 2020

(87) PCT Pub. No.: WO2019/103918
PCT Pub. Date: May 31, 2019

(65) Prior Publication Data
US 2020/0354739 A1    Nov. 12, 2020

Related U.S. Application Data

(60) Provisional application No. 62/589,245, filed on Nov. 21, 2017.

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS 9,029,636 B2 * 5/2015 Wu .................... C12N 15/8218
800/285

FOREIGN PATENT DOCUMENTS

| WO | 2013/092275 A2 | 6/2013 |
| WO | 2014/117988 A1 | 8/2014 |
| WO | 2016/183130 A1 | 11/2015 |

OTHER PUBLICATIONS

Kim et al. Plant Molecular Biology (1994), 24:105-117.*
Thornton et al. Nature structural Biology (2000), structural genomics supplement.*
Gao et al., MPMI, Oct. 2005, 18, 10, 1035-1045.
International Search Report for International Application No. PCT/US18/61411 dated Mar. 26, 2019.
GenBank Accession No. HN847611.1 GS_Ba154104.F GS_Ba Glycine syndetika genomic 5-, genomic survey sequence, Oct. 25, 2010 [online], [Retreived from the Internet: <URL: https://www.ncbi.nlm.nih.gov/nucgss/HN847811.
UniProtKB—K7KQN0 (K7KQN0_SOYBN), Jan. 9, 2013 (online), [Retreived on Jan. 31, 2019], Retrieved from the internet: <URL: https:www.uniprot.org/uniprot/K7KQN0.
Langenbach, Caspar, et al: "Fighting Asian Soybean Rust", Frontiers in Plant Science; vol. 7 Jun. 7, 2016.
Soria-Guerra, Ruth Elena, et al: "Transcriptome analysis of resistant & susceptible genotypes of Glycine tomentella during Phakopsora pachyrhizi infection reveals novel rust resistance genes", Theoretical & Applied Genetics; Int. Jour. of Plant Breeding Res., Springer, Berlin, DE; vol. 120(7), pp. 1315-1318, Jan. 8, 2010 (ISSN: 1432-2242).
Extended European Search Report for PCT/US2018/061411 dated Mar. 18, 2022.

* cited by examiner

*Primary Examiner* — Medina A Ibrahim
(74) *Attorney, Agent, or Firm* — Suparna Kanjilal

(57) ABSTRACT

The present invention relates to methods and compositions for identifying, selecting and/or producing a Disease resistant soybean plant or germplasm using markers, genes and chromosomal intervals derived from *Glycine tomentella* PI441001, PI441008, PI446958, PI583970, or PI483224. A soybean plant or germplasm that has been identified, selected and/or produced by any of the methods of the present invention is also provided. Disease resistant soybean seeds, plants and germplasms are also provided.

40 Claims, 9 Drawing Sheets
Specification includes a Sequence Listing.

FIGURE 4

$$\text{Log}_2\left(\begin{array}{l}\text{Fungal B-tubulin transcripts}\\\text{of construct of interest}\end{array}\right) - \text{Log}_2\left(\begin{array}{l}\text{Fungal B-tubulin transcripts}\\\text{of construct containing GUS}\end{array}\right)$$

RESISTANCE GENES ASSOCIATED WITH DISEASE RESISTANCE IN SOYBEANS

FIELD OF THE INVENTION

The present invention relates to compositions and methods for identifying, selecting and producing enhanced disease and/or pathogen resistant plants using novel resistance genes.

STATEMENT REGARDING ELECTRONIC SUBMISSION OF A SEQUENCE LISTING

An amended Sequence Listing in ASCII text format, submitted under 37 C.F.R. § 1.821, entitled—"81492-WO-L-ORG-NAT-1-Amended2SequenceList_ST25 17.1 MB in size, generated on Dec. 16, 2020 and filed via EFS-Web is provided in lieu of a paper copy. This Sequence Listing is hereby incorporated by reference into the specification for its disclosures.

BACKGROUND

Plant pathogens are known to cause considerable damage to important crops, resulting in significant agricultural losses with widespread consequences for both the food supply and other industries that rely on plant materials. As such, there is a long felt need to reduce the incidence and/or impact of agricultural pathogens on crop production.

Several pathogens have been associated with damage to soybeans, which individually and collectively have the potential to cause significant yield losses in the United States and throughout the world. Exemplary pathogens include, but are not limited to fungi (e.g., genus *Phytophthora* and Asian Soybean rust *Phakopsora pahyrhizi*), nematodes (e.g., genus *Meloidogyne*, particularly, *Meloidogyne javanica*), and soybean stem canker. Given the significant threat to global food supplies that these pathogens present as well as the time and expense associated with treating soybean crops to prevent yield loss, new methods for producing pathogen resistant soybean cultivars are needed. What is needed is novel resistance genes (herein, "R-Genes") that can be introduced into commercial soybean plants to control soybean pathogens.

SUMMARY OF THE INVENTION

This summary lists several embodiments of the presently disclosed subject matter, and in many cases lists variations and permutations of these embodiments.

Compositions and methods for identifying, selecting and producing *Glycine* plants (including wild Glycines (e.g. *Glycine tomentella*) and *Glycine max* lines) with enhanced disease resistance are provided. Disease resistant soybean plants and germplasms are also provided. In some embodiments, methods of producing a disease resistant soybean plant are provided.

In one aspect of the invention there is provided a DNA construct that comprises a promoter that functions in plant cells operably linked to a novel resistance gene ("herein R-Gene). In yet another aspect of the invention there is provided a transgenic plant that contains the DNA construct, wherein the transgenic plant is resistant to soybean pathogens, particularly Asian Soybean Rust.

In another aspect of the invention is a method of preparing a fertile transgenic plant comprising providing a plant expression cassette comprising an R-Gene and contacting recipient plant cells with the plant expression cassette under conditions permitting the uptake of the plant expression cassette by the recipient cells; and selecting the recipient plant cells that contain the plant expression cassette; and regenerating plants from the selected recipient plant cells; and identifying a fertile transgenic plant that is resistant to soybean pathogens, particularly Asian Soybean Rust.

In another aspect of the invention there is provided a fertile transgenic plant that comprises a plant expression cassette comprising an R-Gene and wherein the plant is resistant to soybean pathogens, particularly Asian Soybean Rust.

In another aspect of the invention there is provided a method of controlling ASR in a field comprising the step of planting the seed from a plant comprising an R-gene of the invention.

Thus, it is an object of the presently disclosed subject matter to provide methods for conveying pathogen resistance into non-resistant soybean germplasm or plant lines.

Further the presently disclosed subject matter provides novel *Glycine max* lines comprising in its genome a R-gene that is derived from *Glycine tomentella* and further confers Asian soybean rust resistance (herein, 'ASR') in said novel *Glycine max* line. Soybean plants and/or germplasms identified, produced or selected by the methods of this invention are also provided, as are any progeny and/or seeds derived from a soybean plant or germplasm identified, produced or selected by these methods.

As still a further aspect, the invention encompasses transgenic plants comprising a plant cell, plant part, nucleotide sequence, expression cassette, vector and/or R-genes of the invention.

As a further aspect are seeds that produce the transgenic plants of the invention and seeds produced by the transgenic plants of the invention.

Also provided are harvested products derived from the transgenic plants of the invention, wherein the harvested product optionally comprises a nucleotide sequence, expression cassette, vector and/or R-gene of the invention. Further provided are processed products derived from the harvested products of the invention, wherein the harvested product optionally comprises a nucleotide sequence, expression cassette, vector and/or R-gene of the invention.

Still further, the invention provides as an additional aspect a method of producing a transgenic plant with increased resistance to a soybean pathogen. In embodiments, the method comprises introducing into a plant a polynucleotide, expression cassette, or vector of the invention, wherein the R-gene is expressed in the plant, thereby producing a transgenic plant with increased resistance to a soybean pathogen. Optionally, the introducing step comprises: (i) transforming a plant cell with the polynucleotide, expression cassette or vector and regenerating a transgenic plant; or (ii) crossing a first plant comprising the polynucleotide, expression cassette or vector with a second plant. In embodiments, the method further comprises producing a seed from the transgenic plant. In embodiments, the method further comprises obtaining a progeny plant from the transgenic plant, wherein the progeny plant comprises the polynucleotide, the expression cassette or the vector, expresses the R-gene and has increased resistance to a soybean pathogen.

As yet another aspect, the invention provides a method of producing a transgenic plant with increased resistance to a soybean plant pathogen (e.g., Asian Soybean Rust), the method comprising: (a) planting a seed comprising a polynucleotide, expression cassette or vector of the invention; and (b) growing a transgenic plant from the seed, wherein the transgenic plant comprises the polynucleotide, expression cassette or vector and produces the R-gene and has increased resistance to a soybean pathogen. In embodiments, the method further comprises: (c) harvesting a seed from the transgenic plant of (b), wherein the harvested seed comprises the polynucleotide, expression cassette, vector and/or the R-gene.

Still further, as another aspect, the invention provides a method of producing a seed. In embodiments, the method comprises: (a) providing a transgenic plant that comprises a polynucleotide, expression cassette or vector of the invention; and (b) harvesting a seed from the transgenic plant of (a), wherein the harvested seed comprises the polynucleotide, expression cassette or vector and/or a R-gene of the invention.

The invention further contemplates a method of producing a hybrid plant seed. In representative embodiments, the method comprises: (a) crossing a first inbred plant, which is a transgenic plant comprising a polynucleotide, expression cassette or vector of the invention with a different inbred plant, which may or may not comprise a polynucleotide, expression cassette or vector of the invention; and (b) allowing a hybrid seed to form.

The invention is also drawn to methods of using the polynucleotides of the invention, for example, in DNA constructs or expression cassettes or vectors for transformation and expression in organisms, including plants. The nucleotide or amino acid sequences may be native or synthetic sequences that have been designed for expression in an organism such as a plant.

In embodiments, the invention provides a method of using a polynucleotide, expression cassette or vector of the invention to produce a transgenic seed, where the transgenic seed grows a transgenic plant with increased resistance to a soybean pathogen.

The foregoing and other objects and aspects of the present invention are explained in detail in the drawings and specification set forth below.

BRIEF DESCRIPTION OF THE SEQUENCE LISTING

SEQ ID NOs: 1 & 2 are chromosomal intervals derived from *Glycine tomentella* line accession PI441001 referred to herein as "Scaffold 46840" and "Scaffold 49652" respectively. Scaffold 49652 has been mapped to *G. tomentella* chromosome 5 and Scaffold 46840 has been mapped to *G. tomentella* chromosome 5. SEQ ID NO. 3 is a chromosomal interval derived from *Glycine tomentella* line accession PI 483224 referred to herein as "Scaffold 002687F". Scaffold 002687F has been mapped to *G. tomentella* chromosome 5. SEQ ID NO. 4 is a chromosomal interval derived from *Glycine tomentella* line accession PI 583970 referred to herein as "Scaffold 001084F". Scaffold 001084F has been mapped to *G. tomentella* chromosome 5. SEQ ID NO: 5 is a chromosomal interval derived from *Glycine tomentella* line accession PI583970 herein referred to "Contig 000819F". Contig (000819F has been mapped to *G. tomentella* chromosome 5. Genetic population mapping studies for PI441001, PI483224 and PI 583970 indicate that *Glycine tomentella* Chromosome 5 contains chromosomal intervals highly associated with ASR resistance (e.g. as corresponding to SEQ ID NOs: 1-5). Further data, also indicates that *Glycine tomentella* accessions PI446958, PI499939, PI505220, PI499933, PI441008, PI505256, PI446961 and PI483224 can be used as a source for said chromosomal intervals or genes corresponding to SEQ ID NOs 1-5. These chromosomal intervals or portions thereof may be introduced (i.e. introgressed through use of embryo rescue & marker assisted breeding (MAB)) into *Glycine max* lines to create *Glycine max* lines resistant to various diseases such as ASR. Single nucleotide polymorphisms (SNP) within SEQ ID NOs 1-5 that are associated with ASR resistance are described in PCT Application No. PCT/US2017/036712, published as WO 2017/222827, incorporated herein by reference in its entirety.

Further research into the intervals led to the discovery of causative genes and associated native promoters and terminator sequences were identified from the above interval(s) located or corresponding to on *Glycine tomentella* Chromosome 5.

Figure 1:
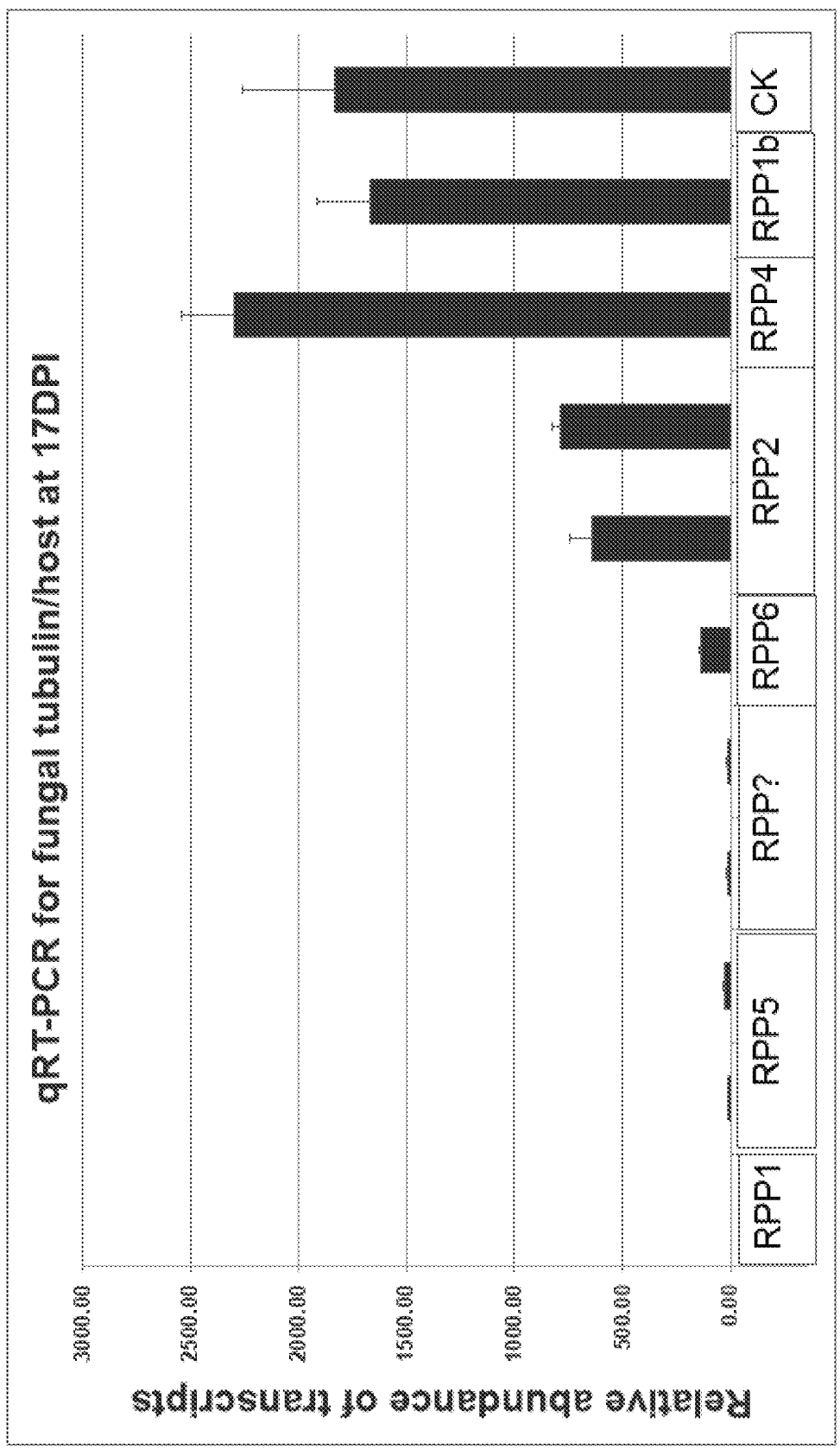
FIG. 1. qRT-PCR measurement of fungal b-tubulin of differential host panel. The measurement correlate well with the phenotypic ratings.
Figure 2:
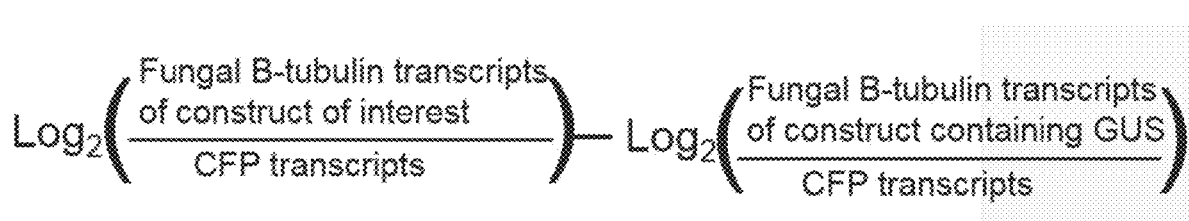
FIG. 2. Formula used to process the qRT-PCR raw reads.
Figure 3:
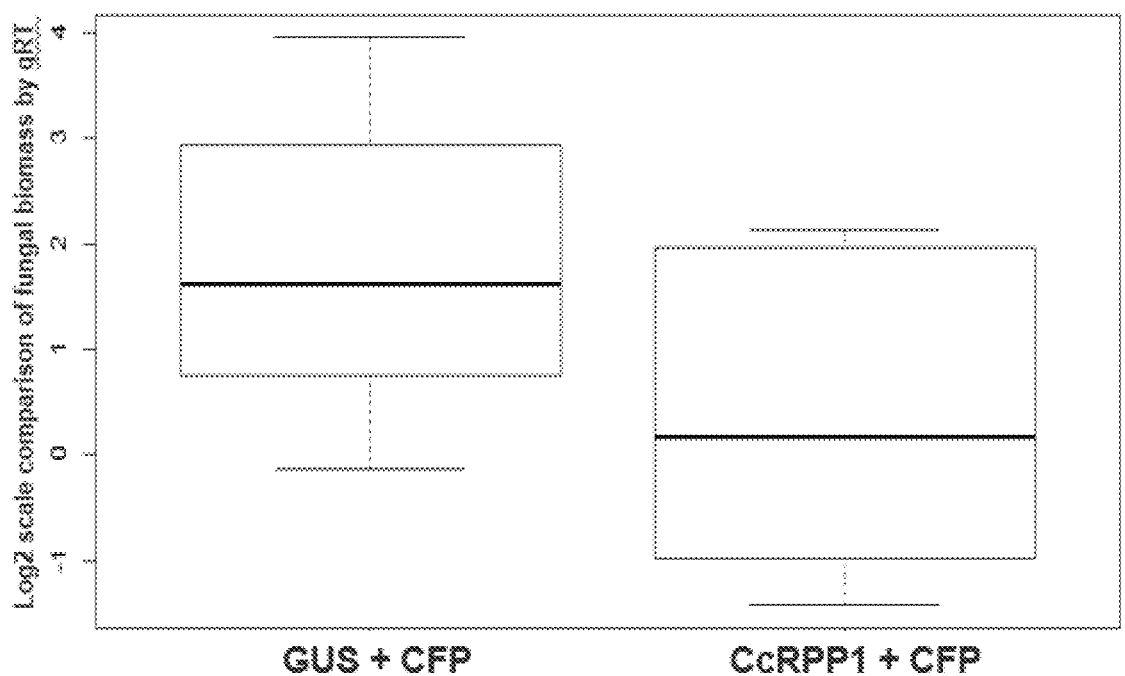
FIG. 3. Normalized fungal biomass with different constructs using known resistance gene CcRpp1 to validate the split leaf system FIG. 4. Alternate formula used to process the qRT-PCR raw reads.
Figure 5:
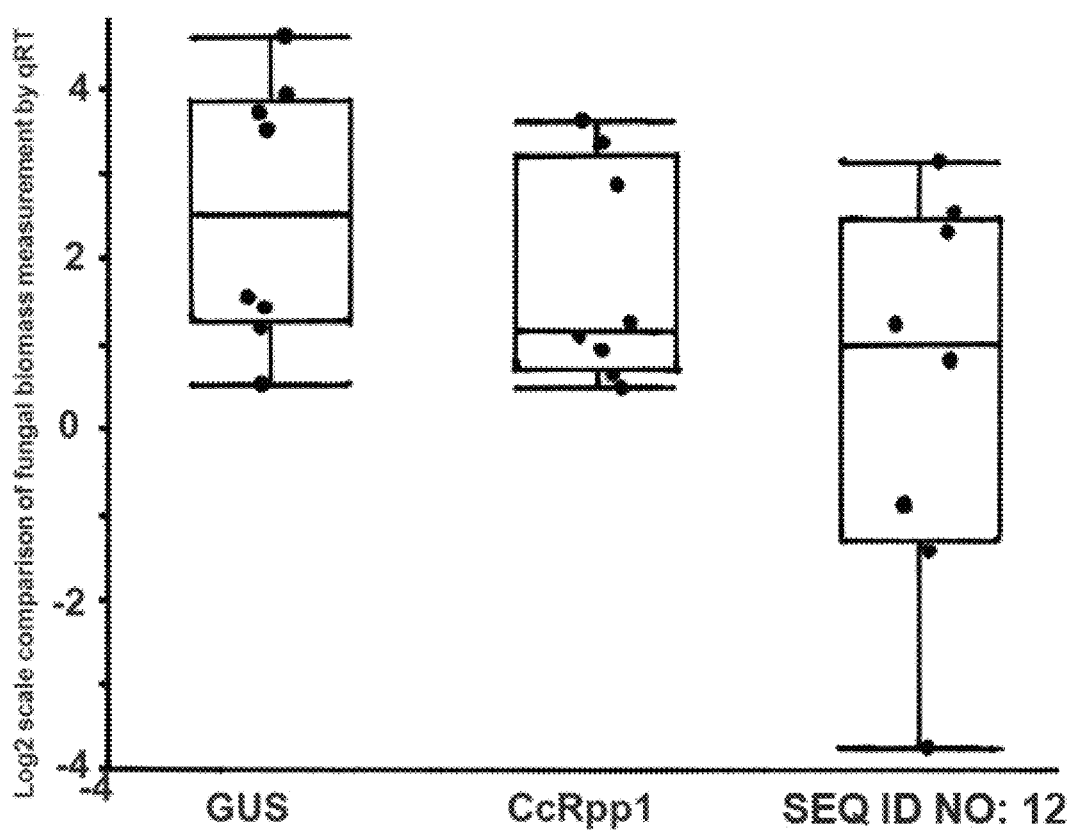
FIG. 5. Split leaf assay validation using CcRpp1, and a construct comprising SEQ ID NO: 12 showed significant disease reduction compared to the check.

SEQ ID NO: 6 is a soy rust resistance gene from PI441001 encoding a protein containing Toll/Interleukin-1 receptor (TIR), nucleotide-binding site (NBS), leucine rich-repeat (LRR), and WKRY domains syntenic to Glyma.05G165800 (Soy_william82_v2) (Herein, a "TNLW" R-gene motif); associated native promoter comprises SEQ ID NO: 7 and terminator sequence comprises SEQ ID NO: 8. SEQ ID NO: 6 encodes the protein of SEQ ID NO: 47.

SEQ ID NO: 9 is a soy rust resistance candidate gene from PI441001 that encodes a protein containing coiled-coiled (CC), nucleotide-binding site (NBS), and leucine rich repeat (LRR) domains. The gene is syntenic to Glyma.05G165600 (Soy_william82_v2) (Herein, a "CNL" R-gene motif); associated native promoter comprises SEQ ID NO: 10 and terminator sequence comprises SEQ ID NO: 11. SEQ ID NO: 9 encodes the protein of SEQ ID NO: 48.

SEQ ID NO: 12 is a soy rust resistance candidate gene from PI583970 that encodes a protein having a CNL R-gene motif; associated native promoter comprises SEQ ID NO: 13 and terminator sequence comprises SEQ ID NO: 14. SEQ ID NO. 12 encodes the protein of SEQ ID NO: 42.

SEQ ID NO: 15 is a soy rust resistance candidate gene from PI583970 that encodes a protein having a CNL R-gene motif; associated promoter used to validate comprises SEQ ID NO: 16 and terminator sequence comprises SEQ ID NO: 17. SEQ ID NO. 15 encodes the protein of SEQ ID NO: 43.

SEQ ID NO: 18 is a soy rust resistance candidate gene from PI583970 that encodes a protein having a CNL R-gene motif; associated promoter used to validate comprises SEQ ID NO: 19 and terminator sequence comprises SEQ ID NO: 20. SEQ ID NO. 18 encodes the protein of SEQ ID NO: 49.

SEQ ID NO: 21 is a soy rust resistance candidate gene from PI446958 that encodes a protein having a CNL R-gene motif; associated promoter used to validate comprises SEQ ID NO: 22 and terminator sequence comprises SEQ ID NO: 23. SEQ ID NO: 21 encodes the protein of SEQ ID NO: 44.

SEQ ID NO: 24 is a soy rust resistance candidate gene from PI446958 that encodes a protein having a CNL R-gene motif; associated native promoter comprises SEQ ID NO: 25 and terminator sequence comprises SEQ ID NO: 26. SEQ ID NO: 24 encodes the protein of SEQ ID NO: 45.

SEQ ID NO: 27 is a soy rust resistance candidate gene from PI446958 that encodes a protein having a CNL R-gene motif; associated promoter used to validate comprises SEQ ID NO: 28 and terminator sequence comprises SEQ ID NO: 29. SEQ ID NO: 27 encodes the protein of SEQ ID NO: 46. Vector Construction for the R-Gene comprising SEQ ID NO: 27 was done using a forward primer comprising SEQ ID NO: 51 and a reverse primer comprising SEQ ID NO: 52.

SEQ ID NO: 30 is a soy rust resistance candidate gene from PI583970 that encodes a protein having a TNLW R-gene motif; associated native promoter comprises SEQ ID NO: 31 and terminator sequence comprises SEQ ID NO: 32. SEQ ID NO: 30 encodes the protein of SEQ ID NO: 50.

Further intervals have been discovered in other *Glycine tomentella* lines as depicted Table 1 below that are associated with ASR resistance and correspond to the intervals described above having/comprising SEQ ID NOs 1-5 and also located on chromosome 5. Interval mapping indicates that ASR resistance can be found in both T1 and T2 *Glycine tomentella* lines. Further, it is contemplated that any of the source lines listed in Table 1 can be used to introduce ASR resistance into elite Soybean plants either by way of plant introgression through embryo rescue or via transgenic expression of genes encoding a protein having a CNL or TNLW R-gene motif or a gene having between 70-100% homology to any of SEQ ID NOs: 6, 9, 12, 15, 18, 21, 24, 27, or 30. Contig/Scaffolds 001082F, 000221F, 000342F, 003716F, 001879F, 001273F, 000866F, 000819F and 49562 are depicted in SEQ ID NOs: 33, 34, 35, 36, 37, 38, 49, 40, and 41 respectively. It is contemplated that homologous sequences with functional ASR resistance genes related to the R-Genes as depicted in SEQ ID NOs: 6, 9, 12, 15, 18, 21, 24, 27 and 30 can be located in the intervals and associated sequences of Table 1.

TABLE 1

Listing of others sources and scaffolds found to comprise intervals associated with increased resistance to Asian Soybean Rust.

| Genome type | Line | Contig/ Scaffold | begin | end |
|---|---|---|---|---|
| T1 | PI505220 | s49652 | 47,538 | 2,464,073 |
| T1 | PI499933 | s49652 | 42,441 | 2,481,008 |
| T1 | PI441008 | 000207F | 1,000,000 | 1,400,000 |
| T1 | PI441008 | 000819F | Whole Contig | Whole Contig |
| T1 | PI441008 | 000866F | Whole Contig | Whole Contig |
| T1 | PI441008 | 001273F | Whole Contig | Whole Contig |
| T1 | PI441008 | 001879F | Whole Contig | Whole Contig |
| T1 | PI441008 | 003716F | Whole Contig | Whole Contig |
| T2 | PI449658 | 000342F | 108,327 | End of contig |
| T2 | PI449658 | 000221F | Whole Contig | Whole Contig |
| T2 | PI449658 | 001082F | Beginning of Contig | 629,163 |

TABLE 1-continued

Listing of others sources and scaffolds found to comprise intervals associated with increased resistance to Asian Soybean Rust.

| Genome type | Line | Contig/ Scaffold | begin | end |
|---|---|---|---|---|
| T2 | PI446961 | 000342F | Whole Contig | Whole Contig |
| T2 | PI446961 | 000221F | Whole Contig | Whole Contig |
| T2 | PI446961 | 001082F | Beginning of Contig | 369,453 |
| T2 | PI505256 | 000342F | 203,123 | End of contig |
| T2 | PI505256 | 000221F | Whole Contig | Whole Contig |
| T2 | PI505256 | 001082F | Beginning of Contig | 326,515 |

DETAILED DESCRIPTION OF THE INVENTION

The presently disclosed subject matter relates to compositions and methods for introducing novel resistance genes (herein, "R-Genes") into commercial soybean plants to control soybean pathogens. The methods involve transforming organisms with nucleotide sequences encoding the R-genes of the invention. The nucleotide sequences of the invention are useful for preparing plants that show increased resistance to soybean pathogens, particularly Asian Soybean Rust (herein, "ASR"). Thus, transformed plants, plant cells, plant tissues and seeds are provided. Compositions include nucleic acids and proteins relating to soybean pathogen resistant plants as well as transformed plants, plant tissues and seeds. Nucleotide sequences of the R-genes and the amino acid sequences of the proteins encoded thereby are disclosed. The sequences find use in the construction of expression vectors for subsequent transformation into plants of interest, as probes for the isolation of other R-genes, and the like.

It is possible to produce soybean pathogen resistant plants by inserting into the plant genome a DNA molecule that provides for resistance (Cook et al, 2012 for SON resistance; Kawashima et al., 2016 for soy rust resistance from pigeon pea).

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), *glycine* (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Definitions

Unless defined otherwise, all technical and scientific terms used herein have the same meaning as commonly understood to one of ordinary skill in the art to which the presently disclosed subject matter belongs.

Although the following terms are believed to be well understood by one of ordinary skill in the art, the following definitions are set forth to facilitate understanding of the presently disclosed subject matter.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount. As used herein, phrases such as "between about X and Y" mean "between about X and about Y" and phrases such as "from about X to Y" mean "from about X to about Y."

As used herein, phrases such as "between about X and Y", "between about X and about Y", "from X to Y" and "from about X to about Y" (and similar phrases) should be interpreted to include X and Y, unless the context indicates otherwise.

A "coding sequence" is a nucleic acid sequence that is transcribed into RNA such as mRNA, rRNA, tRNA, snRNA, sense RNA or antisense RNA. In embodiments, the RNA is then translated to produce a protein.

As used herein, a "codon optimized" nucleotide sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, a nucleotide sequence is codon optimized for the cell (e.g., an animal, plant, fungal or bacterial cell) in which the construct is to be expressed. For example, a construct to be expressed in a plant cell can have all or parts of its sequence codon optimized for expression in a plant. See, for example, U.S. Pat. No. 6,121,014. In embodiments, the polynucleotides of the invention are codon-optimized for expression in a plant cell (e.g., a dicot cell or a monocot cell) or bacterial cell.

The term "comprise", "comprises" or "comprising," when used in this specification, indicates the presence of the stated features, integers, steps, operations, elements, or components, but does not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim "and those that do not materially alter the basic and novel characteristic(s)" of the claimed invention. Thus, the term "consisting essentially of" when used in a claim of this invention is not intended to be interpreted to be equivalent to "comprising."

"Expression cassette" as used herein means a nucleic acid molecule capable of directing expression of at least one polynucleotide of interest, such as a R-gene polynucleotide that encodes protein of the invention, in an appropriate host cell, comprising a promoter operably linked to the polynucleotide of interest which is operably linked to a termination signal. An "expression cassette" also typically comprises additional polynucleotides to facilitate proper translation of the polynucleotide of interest. The expression cassette may also comprise other polynucleotides not related to the expression of a polynucleotide of interest but which are present due to convenient restriction sites for removal of the cassette from an expression vector. In embodiments, at least one of the components in the expression cassette may be heterologous (i.e., foreign) with respect to at least one of the other components (e.g., a heterologous promoter operatively associated with a polynucleotide of interest). The expression cassette may also be one that is naturally occurring but has been obtained in a recombinant form useful for heterologous expression. Typically, however, the expression cassette is heterologous with respect to the host, i.e., the expression cassette (or even the polynucleotide of interest) does not occur naturally in the host cell and has been introduced into the host cell or an ancestor cell thereof by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development (as described in more detail herein). An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

The term "introduced" as used herein, in connection to a plant, means accomplished by any manner including but not limited to; introgression, transgenic, Clustered Regularly Interspaced Short Palindromic Repeats modification (CRISPR), Transcription activator-like effector nucleases (TALENs) (Feng et al. 2013, Joung & Sander 2013), meganucleases, or zinc finger nucleases (ZFNs).

As used herein, the term "wild *glycine*" refers to a perennial *Glycine* plant, for example any one of *G. canescens, G. argyrea, G. clandestine, G. latrobeana, G. albicans, G. aphyonota, G. arenaria, G. curvata, G. cyrtoloba, G. dolichocarpa, G. falcate, G. gracei, G. hirticaulis, G. lactovirens, G. latifolia, G. microphylla, G. montis-douglas,*

*G. peratosa, G. pescadrensis, G. pindanica, G. pullenii, G. rubiginosa, G. stenophita, G. syndetika,* or *G. tomentella.*

As used herein, the term "allele" refers to one of two or more different nucleotides or nucleotide sequences that occur at a specific locus.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced pathogen resistance" refers to a marker whose presence or absence can be used to predict whether and/or to what extent a plant will display a pathogen resistant phenotype (e.g. any favorable SNP allele as described in Tables 1-5 are "associated with" ASR resistance in a soybean plant).

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-53 (1994). The initial cross gives rise to the F1 generation. The term "BC1" refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval defined by and including," used in reference to particular loci and/or alleles, refers to a chromosomal interval delimited by and encompassing the stated loci/alleles.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "desired allele", "favorable allele" and "allele of interest" are used interchangeably to refer to an allele associated with a desired trait (e.g. ASR resistance).

As used herein, the terms "enhanced pathogen resistance" or "enhanced disease resistance" refers to an improvement, enhancement, or increase in a plant's ability to endure and/or thrive despite being infected with a disease (e.g. Asian soybean rust) as compared to one or more control plants (e.g., one or both of the parents, or a plant lacking a marker associated with enhanced pathogen resistance to respective pathogen/disease). Enhanced disease resistance includes any mechanism (other than whole-plant immunity or resistance) that reduces the expression of symptoms indicative of infection for a respective disease such as Asian soybean rust, soybean cyst nematode, Pytophthora, etc.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

An "elite" plant is any plant from an elite line, such that an elite plant is a representative plant from an elite variety. Non-limiting examples of elite soybean varieties that are commercially available to farmers or soybean breeders include: AG00802, A0868, AG0902, A1923, AG2403, A2824, A3704, A4324, A5404, AG5903, AG6202 AG0934; AG1435; AG2031; AG2035; AG2433; AG2733; AG2933; AG3334; AG3832; AG4135; AG4632; AG4934; AG5831; AG6534; and AG7231 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-K2 (NK Division of Syngenta Seeds, Golden Valley, Minn., USA); 90M01, 91M30, 92M33, 93M11, 94M30, 95M30, 97652, P008T22R2; PI6T17R2; P22T69R; P25T51R; P34T07R2; P35T58R; P39T67R; P47T36R; P46T21R; and P56T03R2 (Pioneer Hi-Bred International, Johnston, Iowa, USA); 5G4771NRR and SG5161NRR/STS (Soygenetics, LLC, Lafayette, Ind., USA); S00-K5, S11-L2, S28-Y2, S43-61, S53-A1, S76-L9, S78-G6, S0009-M2; S007-Y4; S04-D3; S14-A6; S20-T6; S21-M7; S26-P3; S28-N6; S30-V6; S35-C3; S36-Y6; S39-C4; S47-K5; S48-D9; S52-Y2; S58-Z4; S67-R6; S73-S8; and S78-G6 (Syngenta Seeds, Henderson, Ky., USA); Richer (Northstar Seed Ltd. Alberta, Calif.); 14RD62 (Stine Seed Co. Ia., USA); or Armor 4744 (Armor Seed, LLC, Ar., USA).

The terms "agronomically elite" as used herein, means a genotype that has a culmination of many distinguishable traits such as emergence, vigor, vegetative vigor, disease resistance, seed set, standability, yield and threshability which allows a producer to harvest a product of commercial significance.

As used herein, the term "commercially significant yield" or "agronomically acceptable yield" refers to a grain yield of at least 100% of a commercial check variety such as AG2703 or DKB23-51.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism.

The terms "nucleic acid," "nucleic acid molecule," "nucleotide sequence," "oligonucleotide" and "polynucleotide" are used interchangeably herein, unless the context indicates otherwise, and refer to a heteropolymer of nucleotides. These terms include without limitation DNA and RNA molecules, including cDNA, genomic DNA, synthetic (e.g., chemically synthesized) DNA and RNA, plasmid DNA, mRNA, antisense RNA, and RNA/DNA hybrids, any of which can be linear or branched, single stranded or double stranded, or a combination thereof. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. In embodiments, the "nucleic acid," "nucleic acid molecule,", "nucleotide sequence,", "oligonucleotide" or "polynucleotide" refer to DNA.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to or "operatively associated" with the nucleotide sequence.

As used herein, the terms "disease tolerance" and "disease resistant" refer to a plant's ability to endure and/or thrive despite being infected with a respective disease. When used in reference to germplasm, the terms refer to the ability of a plant that arises from that germplasm to endure and/or thrive despite being infected with a respective disease. In some embodiments, infected Disease resistant soybean plants may yield as well (or nearly as well) as uninfected soybean plants. In general, a plant or germplasm is labeled as "Disease resistant" if it displays "enhanced pathogen resistance."

As used herein, the term "endogenous" refers to materials originating from within an organism or cell. "Exogenous" refers to materials originating from outside of an organism or cell. This typically applies to nucleic acid molecules used in producing transformed or transgenic host cells and plants.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, a "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the term "genome" as it applies to plant cells encompasses not only chromosomal DNA found within the nucleus, but organelle DNA found within subcellular components of the cell. The term "gene" refers to polynucleic acids that comprise chromosomal DNA, plasmid DNA, cDNA, an artificial DNA polynucleotide, or other DNA that is transcribed into an RNA molecule, wherein the RNA may encode a peptide, polypeptide, or protein, and the genetic elements flanking the coding sequence that are involved in the regulation of expression of the mRNA or polypeptide of the present invention. A "fragment" of a gene is a portion of a full-length polynucleic acid molecule that is of at least a minimum length capable of transcription into a RNA, translation into a peptide, or useful as a probe or primer in a DNA detection method.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm may refer to seeds, cells (including protoplasts and calli) or tissues from which new plants may be grown, as well as plant parts that can be cultured into a whole plant (e.g., stems, buds, roots, leaves, etc.).

As used herein, a "Heterologous DNA" sequence refers to a polynucleotide sequence that originates from a foreign source or species or, if from the same source, is modified from its original form.

As used herein, a "Homologous DNA" refers to DNA from the same source as that of the recipient cell.

As used herein, the term "hybrid" refers to a seed and/or plant produced when at least two genetically dissimilar parents are crossed.

As used herein, the term "Identity" refers to the degree of similarity between two polynucleic acid or protein sequences. An alignment of the two sequences is performed by a suitable algorithm. One widely used and accepted computer program for performing sequence alignments is CLUSTALW v1.6 (Thompson, et al. Nucl. Acids Res., 22: 4673-4680, 1994), although others are commonly used. The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between 200 and 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity. In addition to identity positions, consensus positions are also commonly scored. Consensus amino acids are those known to have similar amino acid properties such as charge, size, polarity, and aromaticity.

As used herein, the term "inbred" refers to a substantially homozygous plant or variety. The term may refer to a plant or variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced ASR tolerance may be introgressed from a donor into a recurrent parent that is not disease resistant. The resulting offspring could then be repeatedly backcrossed and selected until the progeny possess the ASR tolerance allele(s) in the recurrent parent background.

As used herein, an "isolated" nucleic acid molecule is substantially separated away from other nucleic acid sequences with which the nucleic acid is normally associated, such as, from the chromosomal or extrachromosomal DNA of a cell in which the nucleic acid naturally occurs. A nucleic acid molecule is an isolated nucleic acid molecule when it comprises a transgene or part of a transgene present in the genome of another organism. The term also embraces nucleic acids that are biochemically purified so as to substantially remove contaminating nucleic acids and other cellular components. The term "transgene" refers to any polynucleic acid molecule normative to a cell or organism transformed into the cell or organism. "Transgene" also encompasses the component parts of a native plant gene modified by insertion of a normative polynucleic acid molecule by directed recombination or site specific mutation.

A polypeptide is "isolated" if it has been separated from the cellular components (nucleic acids, lipids, carbohydrates, and other polypeptides) that naturally accompany it or that is chemically synthesized or recombinant. A polypeptide molecule is an isolated polypeptide molecule when it is expressed from a transgene in another organism. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Proteins can be purified by any of the means known in the art, for example as described in Guide to Protein Purification, ed. Deutscher, Meth. Enzymol. 185, Academic Press, San Diego, 1990; and Scopes, Protein Purification: Principles and Practice, Springer Verlag, New York, 1982.

Using well-known methods, the skilled artisan can readily produce nucleotide and amino acid sequence variants of genes and proteins that provide a modified gene product. Chemical synthesis of nucleic acids can be performed, for example, on automated oligonucleotide synthesizers. Such variants preferably do not change the reading frame of the protein-coding region of the nucleic acid. The present invention also encompasses fragments of a protein that lacks at least one residue of a full-length protein, but that substantially maintains activity of the protein.

A "locus" is a position on a chromosome where a gene or marker or allele is located. In some embodiments, a locus may encompass one or more nucleotides.

A "non-naturally occurring variety of soybean" is any variety of soybean that does not naturally exist in nature. A "non-naturally occurring variety of soybean" may be produced by any method known in the art, including, but not limited to, transforming a soybean plant or germplasm, transfecting a soybean plant or germplasm and crossing a naturally occurring variety of soybean with a non-naturally occurring variety of soybean. In some embodiments, a "non-naturally occurring variety of soybean" may comprise one of more heterologous nucleotide sequences. In some embodiments, a "non-naturally occurring variety of soybean" may comprise one or more non-naturally occurring copies of a naturally occurring nucleotide sequence (i.e., extraneous copies of a gene that naturally occurs in soybean). In some embodiments, a "non-naturally occurring variety of soybean" may comprise a non-natural combination of two or more naturally occurring nucleotide sequences (i.e., two or more naturally occurring genes that do not naturally occur in the same soybean, for instance genes not found in *Glycine max* lines).

As used herein, the terms "phenotype," "phenotypic trait" or "trait" refer to one or more traits and/or manifestations of an organism. The phenotype can be a manifestation that is observable to the naked eye, or by any other means of evaluation known in the art, e.g., microscopy, biochemical analysis, or an electromechanical assay. In some cases, a phenotype or trait is directly controlled by a single gene or genetic locus, i.e., a "single gene trait." In other cases, a phenotype or trait is the result of several genes. It is noted that, as used herein, the term "disease resistant phenotype" takes into account environmental conditions that might affect the respective disease such that the effect is real and reproducible.

As used herein, the term "plant" may refer to a whole plant, any part thereof, or a cell or tissue culture derived from a plant. Thus, the term "plant" can refer to any of: whole plants, plant components or organs (e.g., roots, stems, leaves, buds, flowers, pods, etc.), plant tissues, seeds and/or plant cells. A plant cell is a cell of a plant, taken from a plant, or derived through culture from a cell taken from a plant. Thus, the term "soybean plant" may refer to a whole soybean plant, one or more parts of a soybean plant (e.g., roots, root tips, stems, leaves, buds, flowers, pods, seeds, cotyledons, etc.), soybean plant cells, soybean plant protoplasts and/or soybean plant calli.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant. In embodiments, the plant cell is non-propagating and/or cannot regenerate a whole plant.

A "plant cell culture" means a culture of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, the term "plant part" includes but is not limited to embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to a DNA amplification method that uses an enzymatic technique to create multiple copies of one sequence of nucleic acid (amplicon). Copies of a DNA molecule are prepared by shuttling a DNA polymerase between two amplimers. The basis of this amplification method is multiple cycles of temperature changes to denature, then re-anneal amplimers (DNA primer molecules), followed by extension to synthesize new DNA strands in the region located between the flanking amplimers. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method known in the art. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066. Primers can be labeled, if desired, by incorporating detectable moieties by for instance spectroscopic, fluorescence, photochemical, biochemical, immunochemical, or chemical moieties. Primers diagnostic (i.e. able to identify or select based on presence of ASR resistant alleles) for ASR resistance can be created to any favorable SNP as described in any one of Tables 1-5. The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). Molecular Cloning: A Laboratory Manual, Third Edition, Cold Spring Harbor Laboratory Press, Cold Spring Harbor, N.Y., United States of America. Generally, lower salt concentration and higher temperature hybridization and/or washes increase the stringency of hybridization conditions.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

The term "promoter" or "promoter region" refers to a polynucleic acid molecule that functions as a regulatory element, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant DNA construct, as demonstrated by its ability to produce mRNA.

A "recombinant" nucleic acid is made by a combination of two otherwise separated segments of nucleic acid sequence, for example, by chemical synthesis or by the manipulation of isolated segments of polynucleic acids by genetic engineering techniques. The term "recombinant DNA construct" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs may be constructed to be capable of expressing antisense RNAs, or stabilized double stranded antisense RNAs.

The phrase "substantially identical," in the context of two nucleic acids or two amino acid sequences, refers to two or more sequences or subsequences that have at least about 50% nucleotide or amino acid residue identity when compared and aligned for maximum correspondence as measured using a sequence comparison algorithm or by visual inspection. In certain embodiments, substantially identical sequences have at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more nucleotide or amino acid residue identity. In certain embodiments, substantial identity exists over a region of the sequences that is at least about 50 amino acid residues, 100 amino acid residues, 150 amino acid residues, 200 amino acid residues, 250 amino acid residues, 300 amino acid residues, 350 amino acid residues, 400 amino acid residues, 450 amino acid residues, 500 amino acid residues, 525 amino acid residues, 526, amino acid residues 527 amino acid residues, 528 amino acid residues, 529 amino acid residues, 530 amino acid residues, 531 amino acid residues, 532 amino acid residues, 533 amino acid residues, 534 amino acid residues, 535 amino acid residues, 536 amino acid residues or more with respect to the protein sequence or the nucleotide sequence encoding the same. In further embodiments, the sequences are substantially identical when they are identical over the entire length of the coding regions.

"Identity" or "percent identity" refers to the degree of identity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally,).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215: 403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules. As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

As used herein, "specifically" or "selectively" hybridizing (and similar terms) refers to the binding, duplexing, or hybridizing of a molecule to a particular nucleic acid target sequence under stringent conditions when that sequence is present in a complex mixture (e.g., total cellular DNA or RNA) to the substantial exclusion of non-target nucleic acids, or even with no detectable binding, duplexing or hybridizing to non-target sequences. Specifically or selectively hybridizing sequences typically are at least about 40% complementary and are optionally substantially complementary or even completely complementary (i.e., 100% identical).

For DNA-DNA hybrids, the $T_m$ can be approximated from the equation of Meinkoth and Wahl, Anal. Biochem., 138: 267-84 (1984): $T_m=81.5°$ C.$+16.6$ (log M)$+0.41$ (% GC)$-0.61$ (% formamide)$-500/L$; where M is the molarity of monovalent cations, % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired degree of identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, highly stringent conditions can utilize a hybridization and/or wash at the thermal melting point ($T_m$) or 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). If the desired degree of mismatching results in a $T_m$ of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M NaPO$_4$, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced.

Expression of an R-Gene Coding Sequence in Plants

DNA constructs are made that contain various genetic elements necessary for the expression of the R-Gene coding sequence in plants. "DNA construct" refers to the heterologous genetic elements operably linked to each other making up a recombinant DNA molecule and may comprise elements that provide expression of a DNA polynucleotide molecule in a host cell and elements that provide maintenance of the construct in the host cell. A plant expression cassette comprises the operable linkage of genetic elements that when transferred into a plant cell provides expression of a desirable gene product. "Plant expression cassette" refers to chimeric DNA segments comprising the regulatory elements that are operably linked to provide the expression of a transgene product in plants. Promoters, leaders, introns, transit peptide encoding polynucleic acids, 3' transcriptional termination regions are all genetic elements that may be operably linked by those skilled in the art of plant molecular biology to provide a desirable level of expression or functionality to an R-gene of the present invention. A DNA construct can contain one or more plant expression cassettes expressing the DNA molecules of the present invention or other DNA molecules useful in the genetic engineering of crop plants.

A variety of promoters specifically active in vegetative tissues, such as leaves, stems, roots and tubers, can be used to express the R-gene polynucleic acid molecules of the present invention.

The translation leader sequence means a DNA molecule located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders, plant virus coat protein leaders, plant rubisco gene leaders among others (Turner and Foster, Molecular Biotechnology 3:225, 1995).

The "3' non-translated sequences" means DNA sequences located downstream of a structural polynucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3'; Fraley et al., Proc. Natl. Acad. Sci. USA 80: 4803-4807, 1983). The use of different 3' non-translated sequences is exemplified by Ingelbrecht et al., Plant Cell 1:671-680, 1989.

The laboratory procedures in recombinant DNA technology used herein are those well-known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al. (1989).

The DNA construct of the present invention may be introduced into the genome of a desired plant host by a variety of conventional transformation techniques that are well known to those skilled in the art. "Transformation" refers to a process of introducing an exogenous polynucleic acid molecule (for example, a DNA construct, a recombinant polynucleic acid molecule) into a cell or protoplast and that exogenous polynucleic acid molecule is incorporated into a host cell genome or an organelle genome (for example, chloroplast or mitochondria) or is capable of autonomous replication. "Transformed" or "transgenic" refers to a cell, tissue, organ, or organism into which a foreign polynucleic acid, such as a DNA vector or recombinant polynucleic acid molecule. A "transgenic" or "transformed" cell or organism also includes progeny of the cell or organism and progeny produced from a breeding program employing such a "transgenic" plant as a parent in a cross and exhibiting an altered phenotype resulting from the presence of the foreign polynucleic acid molecule.

Methods of transformation of plant cells or tissues include, but are not limited to Agrobacterium mediated transformation method and the Biolistics or particle-gun mediated transformation method. Suitable plant transformation vectors for the purpose of Agrobacterium mediated transformation include-those elements derived from a tumor inducing (Ti) plasmid of Agrobacterium tumefaciens, for example, right border (RB) regions and left border (LB) regions, and others disclosed by Herrera-Estrella et al., Nature 303:209 (1983); Bevan, Nucleic Acids Res. 12:8711-8721 (1984); Klee et al., Bio-Technology 3(7):637-642 (1985). In addition to plant transformation vectors derived from the Ti or root-inducing (Ri) plasmids of Agrobacterium, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

DNA constructs can be prepared that incorporate the R-gene coding sequences of the present invention for use in directing the expression of the sequences directly from the host plant cell plastid. Examples of such constructs suitable for this purpose and methods that are known in the art and are generally described, for example, in Svab et al., Proc. Natl. Acad. Sci. USA 87:8526-8530, (1990) and Svab et al., Proc. Natl. Acad. Sci. USA 90:913-917 (1993) and in U.S. Pat. No. 5,693,507.

When adequate numbers of cells containing the exogenous polynucleic acid molecule encoding polypeptides from the present invention are obtained, the cells can be cultured, then regenerated into whole plants. "Regeneration" refers to the process of growing a plant from a plant cell (for example, plant protoplast or explant). Such regeneration techniques rely on manipulation of certain phytohormones in a tissue culture growth medium, typically relying on a biocide and/or herbicide marker that has been introduced together with the desired nucleotide sequences. Choice of methodology for the regeneration step is not critical See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Such regeneration techniques are described generally in Klee et al., Ann. Rev. Plant Phys. 38:467-486 (1987).

The development or regeneration of transgenic plants containing the exogenous polynucleic acid molecule that encodes a polypeptide of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants.

Disease Resistant Soybean Plants and Germplasms

The present invention provides disease resistant soybean plants and germplasms. A Disease resistant soybean plant or germplasm may be produced by any method whereby an R-gene is introduced into the soybean plant or germplasm, including, but not limited to, transformation, protoplast transformation or fusion, a double haploid technique, embryo rescue, gene editing and/or by any other nucleic acid transfer system.

In some embodiments, the soybean plant or germplasm comprises a non-naturally occurring variety of soybean. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The disease resistant soybean plant or germplasm may be the progeny of a cross between an elite variety of soybean and a variety of soybean that comprises an R-gene for enhanced Disease tolerance (e.g. ASR) wherein the R-gene is selected from the group consisting of genes encoding a protein having a CNL or TNLW R-gene motif or a gene having between 70-100% homology to any of SEQ ID NOs: 6, 9, 12, 15, 18, 21, 24, 27, or 30.

The disease resistant soybean plant or germplasm may be the progeny of an introgression wherein the recurrent parent is an elite variety of soybean and the donor comprises an R-gene associated with enhanced disease tolerance and/or resistance wherein the donor carries a gene encoding a protein having a CNL or TNLW R-gene motif or a gene having between 70-100% homology to any of SEQ ID NOs: 6, 9, 12, 15, 18, 21, 24, 27, or 30.

The disease resistant soybean plant or germplasm may be the progeny of a cross between a first elite variety of soybean (e.g., a tester line) and the progeny of a cross between a second elite variety of soybean (e.g., a recurrent parent) and a variety of soybean that comprises an R-gene.

A disease resistant soybean plant and germplasm of the present invention may comprise one or R-genes of the present invention (e.g. any any of SEQ ID NOs: 6, 9, 12, 15, 18, 21, 24, 27, or 30).

Disease Resistant Soybean Seeds

The present invention provides disease resistant soybean seeds. As discussed above, the methods of the present invention may be utilized to identify, produce and/or select a disease resistant soybean seed. In addition to the methods described above, a disease resistant soybean seed may be produced by any method whereby an R-gene is introduced into the soybean seed, including, but not limited to, transformation, protoplast transformation or fusion, a double haploid technique, embryo rescue, genetic editing (e.g. CRISPR or TALEN or MegaNucleases) and/or by any other nucleic acid transfer system.

In some embodiments, the disease resistant soybean seed comprises a non-naturally occurring variety of soybean. In some embodiments, the soybean seed is at least about 50%, 55%, 60%, 65%, 70%, 75%, 80%, 85%, 90%, 95%, 97%, 99% or 100% identical to that of an elite variety of soybean.

The disease resistant soybean seed may be produced by a disease resistant soybean plant identified, produced or selected by the methods of the present invention.

A disease resistant soybean seed of the present invention may comprise, be selected by or produced by use of one or more R-genes of the present invention.

The embodiments of the invention include the following:

EXAMPLES

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

Example 1 Identification of ASR Resistant Wild Glycine Lines

Multiple wild glycine (Glycine tomentella) lines were evaluated for ASR resistance against sixteen rust strains collected across a diverse range of environments. The rust data were generated using single pustule derived isolates from USDA-ARS (FL Q09, FL Q12, LABR13, FLQ11) and field populations (FL Q15, FLQ16, RTP1, RTP2, Vero, BR01, BR02 and BR03), the screening was carried out in contained facilities. Of the Glycine tomentella lines screened for ASR resistance, the following Glycine tomentella lines showed broad resistance against all ASR strains tested: PI441001, PI483224, PI583970, PI446958, PI499939, PI505220, PI499933, PI441008, PI505256 or PI446961.

Figure 6:
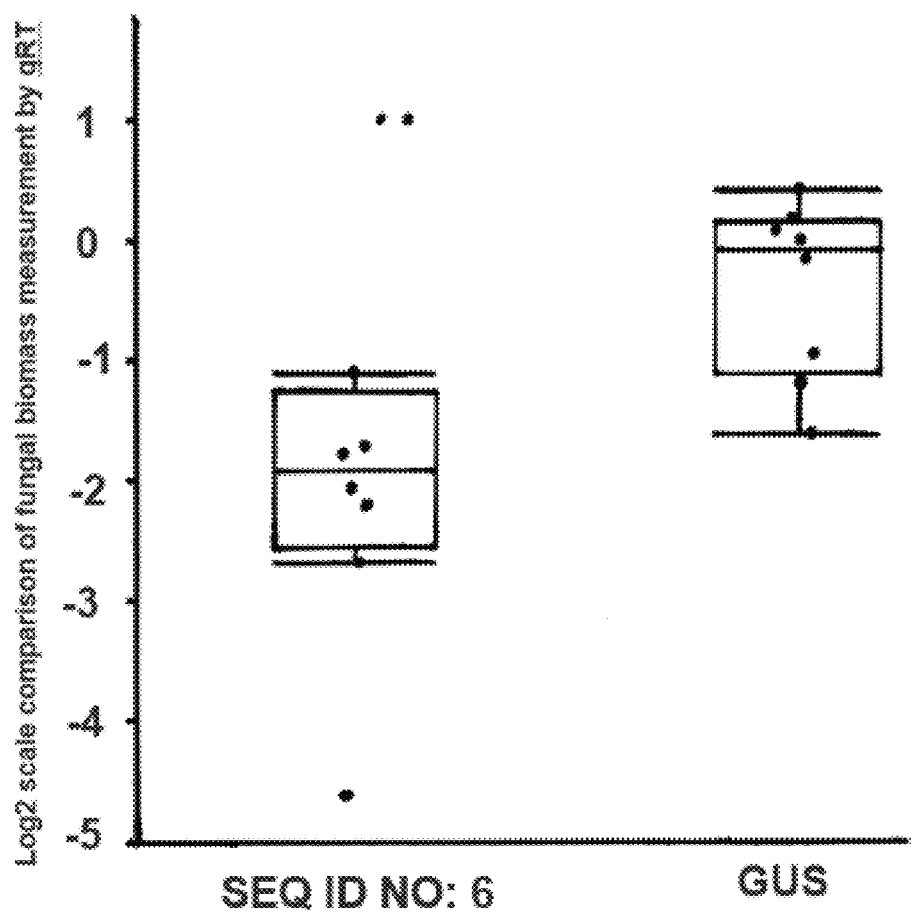
FIG. 6. Split leaf assay validation of SEQ ID NO: 6 showing significant disease reduction compared to check.

Each Glycine tomentella line was evaluated over a multiple day course of infection and rated at various time points using a rust rating scale based on groupings modified from Burdon and Speer, T A G, 1984 (see FIG. 6). Each Glycine tomentella accession was screened >2 times with ~4 plants each time in using a large diverse panel of rust isolates.

Figure 7:
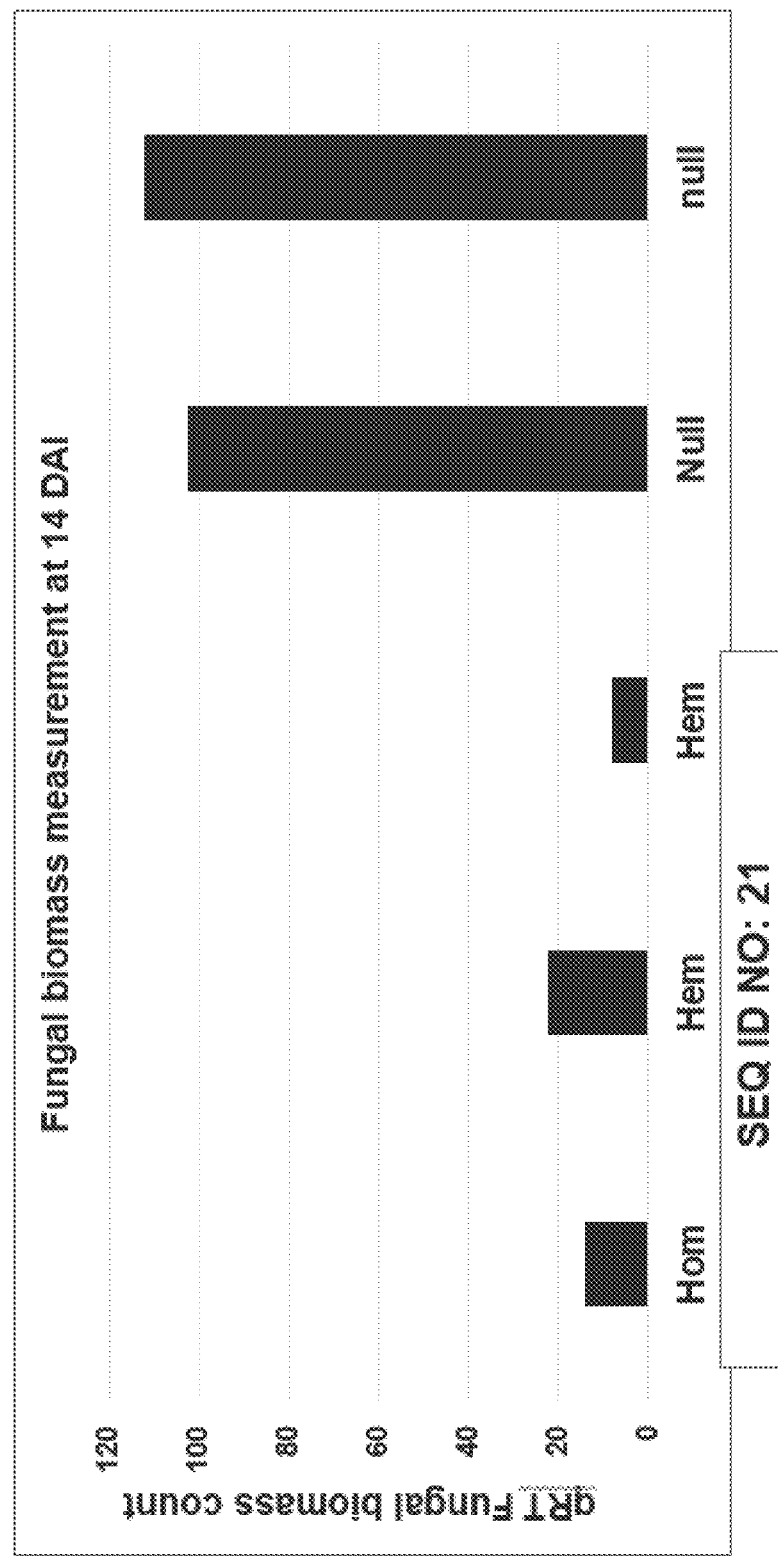
FIG. 7. Stable transformation (T1 events) results showing three events carrying SEQ ID NO: 21 delivering about 80% disease control. The bar is graphed as average of fungal b-tubulin transcripts FIG. 8. Stable transformation (T0 events) results showing two events carrying SEQ ID NO: 27 conferring resistance to soybean rust.
Figure 8:
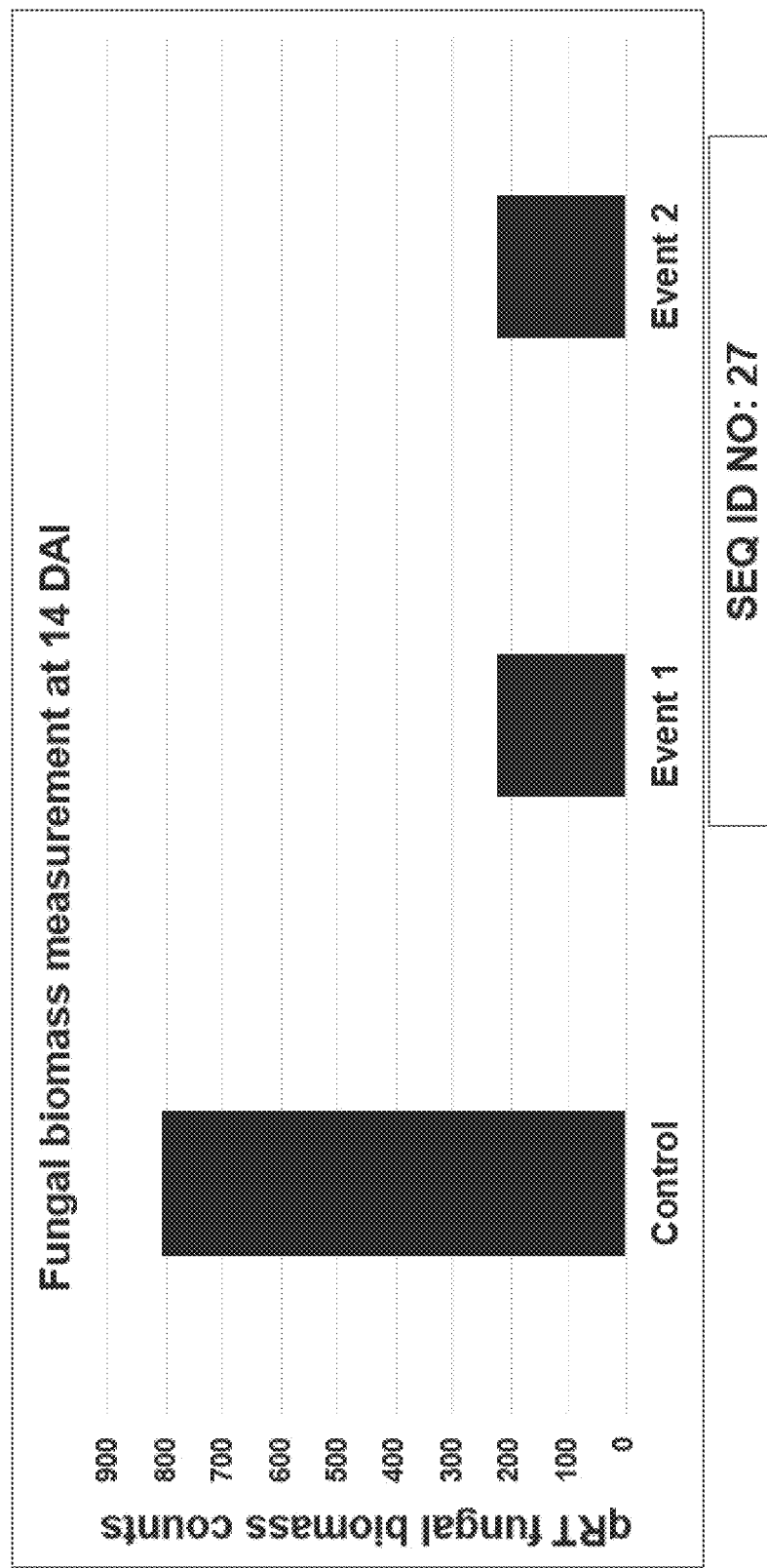
Figure 9:
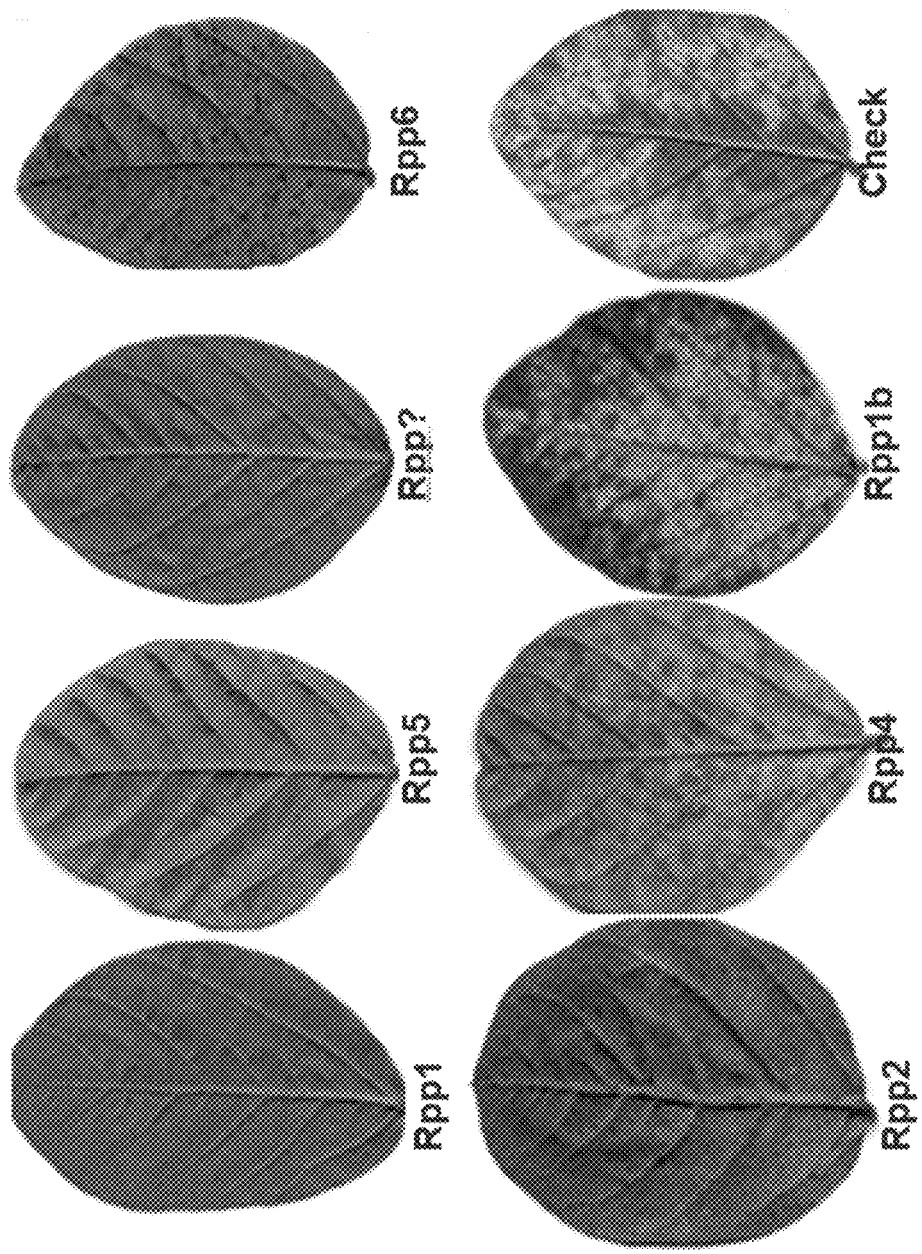
FIG. 9. Foliar symptoms correlating to qRT assay.

Example 2 Allele Mining & Associations to PI441001, PI441008, PI446958, PI583970, or PI483224 ASR Loci Resistant parent lines (i.e. PI441001, PI441008, PI446958, PI583970, and PI483224) were crossed with a susceptible Glycine tomentella line and F1 plants were generated (See Table 2). F1 plants were self-fertilized to generate F2 seed. F2 seed was harvested from the selfed F1 plant. Around 200 F2 seed were sown and leaf tissue from each plant was collected for genotyping studies. Each line was inoculated with Phakopsora pachyrhizi to determine the resistance/susceptible phenotype of each F2 individual. Tissue from 50 resistant F2s and 50 susceptible F2s were combined in separate pools and genomic DNA was prepared from each pool. Illumina sequencing libraries were prepared from DNA for each of the pools and each library was sequenced in two Illumina HiSeq2000 2×100 bp Paired-End (PE) lanes. The average yield per sample was 383 million read pairs, which equals 77 gigabases of sequence per library. The sequencing reads were trimmed to remove bases with PHRED quality scores of <15.

Quality trimmed reads were aligned to the PI441001, PI441008, PI583970, and PI483224 reference genome sequence using GSNAP (WU and NACU 2010) as paired-end fragments. If a pair of reads could not be aligned together, they were treated as singletons for alignment. Reads were used in subsequent analyses if they mapped uniquely to the reference (≤2 mismatches every 36 bp and less than 5 bases for every 75 bp as tails).

SNPs were filtered prior to BSA analysis based on read depth, with SNPs having between 40 and 200× read depth being retained. A Chi-square test was used to select SNPs with significantly different read counts between the two alleles in the two pools. An empirical Bayesian approach (LIU et al. 2012) was used to estimate the conditional probability that there is no recombination between each SNP marker and the causal locus in both the resistant pool and in the susceptible pool. The probability of the linkage between the SNP and the causal gene is the geometric mean of these two conditional probabilities. Around 1000 SNPs were found to have possible linkage to the target locus. A subset of these putatively linked SNPs were used to fine map the locus using phenotyped F2 individuals. See references: LIU, S., C.-T. YEH, H. M. TANG, D. NETTLETON AND P. S. SCHNABLE, 2012 Gene Mapping via Bulked Segregant RNA-Seq (BSR-Seq). PLoS ONE 7: e36406 & Wu, T. D., and S. Nacu, 2010 Fast and SNP-tolerant detection of complex variants and splicing in short reads. Bioinformatics 26: 873-881.

TABLE 2

| Plant Crossings and Study Type | | | | |
|---|---|---|---|---|
| Species | PI# (male) | PI # (female) | Genome Size (Gb) | F2: Resistant to Susceptible Ratio |
| *G. tomentella* | PI441001 | PI441010 | 2 | 3:1 |
| *G. tomentella* | PI441001 | PI441011 | 2 | 3:1 |
| *G. tomentella* | PI441001 | PI441010 | 2 | 3:1 |
| *G. tomentella* | PI583970 | PI441007 | 2 | 3:1 |
| *G. tomentella* | PI583970 | PI441010 | 2 | 3:1 |
| *G. tomentella* | PI583970 | PI441011 | 2 | 3:1 |
| *G. tomentella* | PI448224 | PI441010 | 2 | 3:1 |
| *G. tomentella* | PI441008 | PI441010 | 2 | 7:9 |

1. PI441001 Data2Bio LLC (Ames, Iowa) Lab Methodology for gBSA-Seq Analysis for Tetraploid Soybean.

Chromosome discovery for causal loci in the tetraploid soybean population, PI441001 was carried out using Data2Bio's Genomic Bulked Segregant Analysis (gBSA) technology. It was theorized that ASR resistance is controlled by a single dominant allele. Four libraries were generated from DNA samples extracted from two susceptible tissue pools and two resistant tissue pools. These pools were then sequenced in eight (8) Illumina HiSeq2000 2×100 bp Paired-End (PE) lanes. A summary of the reference genomes used for subsequent analyses, read processing from raw data to quality trimming, alignment, SNP discovery and SNP impact are demonstrated in FIGS. 1-5 for population 441001. After various filtering steps 110,503 informative SNPs were identified in the PI441001 genome as being significantly associated with ASR resistance. A Bayesian approach was then used to calculate trait-associated probabilities. Next, physical maps of trait-associated SNPs (probability cutoff at 0.01) for the top contigs were created (FIG. 1). Two scaffolds, 46840 and 49652, were identified in PI441001 (SEQ ID NOs: 1 and 2 respectively). SNPs from these enriched scaffolds were mapped to the public *Glycine max* genome. In both populations, most of the SNPs from the top scaffolds clustered on small portions of Chr05 and Chr08 (see FIG. 4).

2. PI583970 Data2Bio LLC (Ames, Iowa) Lab Methodology for gBSA-Seq Analysis for Tetraploid Soybean Chromosome discovery for loci in the tetraploid soybean population, PI583970 was carried out using Data2Bio's Genomic Bulked Segregant Analysis (gBSA) technology. Two libraries were created from RNA samples extracted from one susceptible tissue pool and one resistant tissue RNA pool. After various filtering steps 59,014 informative SNPs were identified in the PI583970 genome that were significantly associated with ASR resistance. A Bayesian approach was then used to calculate trait-associated probabilities. Next, a physical map of trait-associated SNPs on contigs was created. The clustering of these SNPs suggests that the resistance loci is located in or near scaffold 000819F (see FIG. 7; Scaffold 001084F is SEQ ID NO: 4). The context sequences associated with these SNPs were also aligned to the public *Glycine max* genome to create a chromosome-level understanding of the mapping interval. The chromosomal positions of the trait-associated (ASR resistance) SNPs were then displayed graphically. Most of the SNPs from scaffold 001084F mapped and clustered on a small region of Chr05 (see FIG. 8). The data suggest that the loci responsible for ASR resistance maps within or near the interval 0.11 to 0.30 Mbp on scaffold 001084F (FIG. 9).

3. PI483224 Data2Bio LLC (Ames, Iowa) Lab Methodology for gBSA-Seq Analysis for Tetraploid Soybean Chromosome discovery for causal loci in the tetraploid soybean population, PI483224 was carried out using Data2Bio's Genomic Bulked Segregant Analysis (gBSA) technology. Two libraries were created from DNA samples extracted from one susceptible tissue pool and one resistant tissue pool (PI483224). After various filtering steps 428,263 informative SNPs were identified in the PI483224 genome to be significantly associated with ASR resistance. A Bayesian approach was then used to calculate trait-associated probabilities. Next, a physical map of trait-associated SNPs on contigs was created. The clustering of these SNPs indicates that the ASR resistance loci is located on or near scaffold 002687F (see FIG. 10). The context sequences associated with these SNPs were also aligned to the public *Glycine max* genome to create a chromosome-level understanding of the mapping interval. The chromosomal positions of the trait-associated (ASR resistant) SNPs were displayed graphically. Most of the SNPs from scaffold 002687F mapped to a small region of Chr05 (See FIG. 11). Data indicates that the ASR loci may map within or near the interval 0.17 to 0.36 MB on scaffold 002687F (see FIG. 12 and SEQ ID NO: 3).

Example 3 Embryo Rescue & Introgression of R Gene Intervals into *Glycine max* Lines Embryo rescue is performed (as described below) and chemical treatment to induce chromosome doubling is applied in order to generate amphidiploid shoots. If the amphidiploid plants are fertile they will be used to backcross with *Glycine max*. Backcrossing with *Glycine max* and subsequent embryo rescue will need to be performed for several generations in order to gradually eliminate the perennial *Glycine tomentella* chromosomes eventually resulting in ASR resistant *Glycine max* plant Wide crosses were carried out using Elite Syngenta soybean (*Glycine max*) lines (RM 3.7 to 4.8). The elite soybean lines are used as the females (pollen recipients) and multiple accessions of *Glycine tomentella* are used as the males or pollen donors. Selecting flowers from the *Glycine tomentella* plant containing anthers at the proper developmental stage is important. New, fully-opened, brightly colored flowers hold anthers with mature pollen. The pollen should appear as loose, yellow dust. These flowers are removed from the *Glycine tomentella* plant and crossed with the elite *Glycine max* plant for pollination. Pollen from the *Glycine tomentella* plants should be used within 30 minutes of flower removal. It is also important to identify and select elite soybean flower buds that are ready for pollination. A soybean flower bud is generally ready when it is larger in size when compared to an immature bud. The sepals of the soybean blossoms are lighter in color and the petals are just beginning to appear. First, use a pair of fine-tipped tweezers to carefully detach the sepals from the flower bud to expose the outer set of petals. Then, gently grasp and remove the petals (5 in total) from the flower exposing the ring of stamens surrounding the pistil. Since the stigma is receptive to pollen 1 day before the anthers begin shedding pollen it is important to recognize the stage development of "female ready, male not ready". When pollinating soybean flowers at this developmental stage it is not necessary to emasculate the female flower. Locate the stigma on the elite soybean flower. Then using 1 male flower, carefully peel off the petals to expose the anthers and gently dust the pollen grains onto the stigma of the soybean flower. Care should be taken not to damage the stigma at any time during this process. Starting the day after pollination a hormone mixture is sprayed onto the pollinated flower and eventual developing F1 pod 1× every day until harvest. The pollinated flower or pod is saturated with a light mist of the hormone mixture, taking care not to cause the flower/pod to prematurely detach from the plant. The mixture contains 100 mg GA3, 25 mg 1-Naphthaleneacetic acid (NAA) and 5 mg kinetin/L distilled water. Application of these hormones aid in the retention of the developing pod and in increased pod growth. The above described wide cross methodology results in success rates significantly higher than that reported in the literature. Further, no emasculation of female flowers is necessary, which saves time and reduces risk of damage to the stigma.

Harvest: Pods from wide crosses are harvested at approximately 14 to 16 days post pollination. (Harvest dates in the literature suggest 19 to 21 days, however the above method allows for faster harvest time and more robust pods.). Pods are collected and counted according to wide cross combination to determine crossing success. The average crossing success across multiple soybean females and 5 different accessions of *Glycine tomentella* is approximately 40%. The wide cross pods can contain 1 to 3 seeds but generally 2 seeds are found in each F1 pod. The above described methodology allows for pod harvest at 14 to 16 days after pollination, ~5 days earlier than described in literature.

Embryo rescue: Harvested pods are collected and brought back to the lab to be sterilized. The pods are first rinsed with 70% EtOH for 2 to 3 minutes and then placed in 10% Clorox bleach for an additional 30 minutes on a platform shaker at approximately 130 RPM. Finally, the pods are rinsed multiple times with sterile water to remove any residual bleach. Embryo isolation can begin immediately following pod sterilization or pods can be stored at 4° C. for up to 24 hours prior to embryo isolation. The sterilized pods are next taken to a laminar flow hood where the embryos can be rescued. Individual pods are placed in a sterile petri dish and opened using a scalpel and forceps. An incision is made along the length of the wide cross pod away from the seed. The pod can then be easily opened to expose the seed. Alternatively, two pair of forceps can be used to separate the pod shell. Carefully remove the seed from the pod and place in a sterile petri dish under a dissection microscope. Very fine forceps are needed to isolate the embryo from the seed. With forceps in one hand, gently hold the side of the seed away from the embryo, with the hilum facing up. Use another pair of forceps in the other hand to remove the seed coat from the side of the seed containing the embryo. Peel off the membrane surrounding the embryo and push the embryo up from its bottom side. Embryos should be past the globular developmental stage and preferably past the early heart developmental stage (middle to late heart stage, cotyledon stage and early maturation stage embryos are desired). Isolated embryos are transferred to embryo rescue medium such as Soy ER1-1 (i.e. 3.1 g B5 basal salt, Gamborg's, 1 ml B5 vitamins 1000×, 40 g sucrose [C12H22O11], 0.25 g casein hydrolysate, 0.25 ml BAP, 0.75 g MgCl2*6H2O, 20 ml glutamine 25 mg/ml, 0.1 g serine [C3H7NO3], 4 ml Asparagine 25 mg/ml and 0.05 ml of IBA 1 mg/ml) Murashige and Skoog Medium (MS) and Gamborg's B-5 media (Bridgen, 1994) may also be used as embryo rescue medium. Embryos can be treated to induce chromosome doubling at this time. (See below for chromosome doubling details.) Isolated embryos remain on embryo rescue medium for 21 to 30 days at 24° C. Embryos may remain in the dark for the entire incubation on ER1-1, they also can be incubated in the dark and later completed in the light, or may spend the entire incubation in the light. There is not a callus induction stage in this protocol, shoots are developed directly from the embryos which allows for faster turnaround time, plantlet survival and better quality results. The above described embryo rescue method involves direct shoot regeneration from embryos, rather than regeneration through embryogenesis, thus making plant recovery quicker (shoot recovery in approximately 2-3 months, compared to reported up to 1 year timeline in the literature). Further, the following protocol does not require culture in the dark following transfer to germination medium nor does the above protocol require a transfer to rooting medium.

Chromosome doubling treatments: Either colchicine of trifluralin can be used to induce chromosome doubling. Ideally, late heart stage wide cross embryos (or larger) are chemically treated to induce chromosome doubling at any time from immediately following isolation up to 1 week post isolation. The doubling agent can be mixed in either solid or liquid medium and applied for several hours or up to a few days. Trifluralin is used at a concentration of 10-40 uM in either solid or liquid media. Alternatively, colchicine is used at a concentration of 0.4-1 mg/ml in either solid or liquid media. Following chemical treatment, embryos are transferred to fresh embryo rescue medium.

Shoot regeneration: Developing embryos are transferred from rescue medium to germination medium such as Soy ER GSMv2 (i.e. 3.2 g Schenk and Hilderbrandt Basal salt mixture, 1 g Myo-inositol [C6H12O6], 5 ml Thiamine 1 mg/ml, 0.5 ml pyridoxine 1 mg/ml, 10 g sucrose [C12H22O11], and 7.5 g purified agar) for approximately 3 to 5 weeks in the light at 24° C. Alternatively, developing embryos may be transferred from rescue medium to elongation medium such as Soy E1 0 No TCV (i.e. 4.3 g MS Basal salt Mixture [MSP01], 5 ml MS iron 200×, 30 g Sucrose [C12H22O11], 1 g MES [C6H13NO4S], 8 g purified agar, 1 ml B5 vitamins 100×, 2 ml glutamine 25 mg/ml, 0.50 ml zeatin riboside, trans isomers 1 mg/ml, 0.1 ml IAA 1 mg/ml, 0.2 ml GA3 5 mg/ml, 1.5 ml timentin 100 mg/ml, 0.3 ml cefotaxime 250 mg/ml, 0.5 ml vancomycin 100 mg/ml) Shoots can be kept on medium for approximately 3 to 5 weeks in the light at 24° C. Developing shoots may be transferred from media plates to Phytocons containing either germination or elongation medium for further shoot development. Established shoots having suitable roots are moved to soil.

Ploidy Analysis: Ploidy analysis is conducted using a flow cytometer. Leaf tissue for ploidy analysis is collected from small shoots either in culture or after establishment in soil. Tissue is collected on dry ice and stored at −80° C. until analysis, or collected on wet ice and analyzed the same day. A sample size of 0.5 cm$^2$ is sufficient. Samples are prepared according to the instructions in the Sysmex kit (Sysmex Inc., Kobe Japan). Each sample set contains an untreated F1 plant (not treated to induce chromosome doubling) as a control.

Example 4 ASR Resistance Trait Introgression

Amphidiploid lines generated from the wide cross (i.e. *Glycine tomentella* crossed with *Glycine max*) followed by embryo rescue as described in Example 3 were backcrossed multiple times with a recurrent elite *Glycine max* lines. It is known in the art that multiple backcrosses are needed to generate fertile hybrid lines, in particular the literature suggests that a BC3 generation is necessary. In this case it was determined that an additional backcrosses are necessary, BC4 in the case of *G. tomentella x G. max* to generate fertile hybrid plants. F1 hybrid plants produced by the methods as described above were created from wide crosses comprising PI441001, PI441008, PI446958, PI583970, and PI483224. F1 plants were next crossed as a female with a male recurrent *G. max* plant to perform a first backcross (BC1 progeny). BC1 Progeny were further backcrossed for multiple generations (e.g. BC2). BC plants are evaluated for ASR resistance, chromosome numbers and in some cases lines are genotyped through use of molecular markers as described herein to detect the presence of chromosome intervals corresponding to SEQ ID NOs 1-5 or any marker identified in Tables 1-5.

Example 5 Identification of Two Causative Genes Located within *G. tomentella* Chromosome 5 Intervals Further genotyping of the various *G. tomentella* intervals led to the discovery of two causative genes for ASR resistance located on chromosome 5 within the disclosed intervals. A first gene type encodes a TNLW R-gene motif and is depicted in SEQ ID NOs 6 and 30 located from PI441001 and PI583970 respectively. A second gene type located in the discovered intervals encodes a CNL R-gene motif and is depicted in SEQ ID NOs 9, 12, 15, 18, 21, 24, and 27. It is contemplated that any of these genes or homologs thereof can be employed in a transgenic, gene editing or breeding method utilizing embryo rescue as described above to generate plants having increased resistance to ASR.

Example 6 Construction of Vectors Comprising R-Genes

Constructs were generated comprising each of the R-genes described in Example 5 above.

a) Vector Construction for R-Gene Comprising SEQ ID NO: 6

Vector type: Binary Vector

Construct Size (bp): 30,982

Functional description: A binary vector for soybean transformation with ALS selection, harboring gGtoRG1-01, a candidate soy rust resistance gene encoding a protein containing Toll/Interleukin-1 receptor (TIR), nucleotide-binding site (NBS), leucine rich-repeat (LRR), and WKRY domains syntenic to Glyma.05G165800 (Soy_william82_v2).

Cloning methods: GenScript synthesized RG1 as four fragments RG1-PartI, -PartII, -PartIII and -PartIV [U9490BJ270-1 (23950), U9490BJ270-2 (23952), U9490BJ270-3 (23953), and U9490BJ270-4 (23954)]. The first and last 2 fragments were cloned into the bridge vector 21177 through SanDI/ScaI, ScaI/RsrII, respectively to obtain the intermediates 21177-PartI+II and 21177 Part-III+

IV. Then the PartI+II (SanDI/ScaI), PartIII+IV (ScaI/RsrII) in the two intermediates were all cloned into 22296 at once through three way ligation at SanDI site of 22296. The positive clone was confirmed by digestion with Alw44I/NheI/SalI and by sequencing over the cloning junctions (SYN04455:65-78).

Sequences used include SEQ ID NO. 6 (coding sequence), SEQ ID NO. 7 (promoter) and SEQ ID NO. 8 (terminator). SEQ ID NO: 6 encodes the protein of SEQ ID NO: 47.

b) Vector Construction for R-Gene Comprising SEQ ID NO: 9

Vector type: Binary Vector
Construct Size (bp): 17,713
Functional description: A binary vector for soybean transformation with the ALS selection harboring a soy rust resistance candidate gene that encodes a protein containing coiled-coiled (CC), nucleotide-binding site (NBS), and leucine rich repeat (LRR) domains. The gene is syntenic to Glyma.05G165600 (Soy_william82_v2).

Cloning methods: GenScript synthesized RG2 as two fragments PartI (SanDI/SacI, U1935CD120-1, 24076) and PartII (SacI/RsrII, U1935CD120-2, 24077), and ligated into 22296 at SanDI. The positive clone was confirmed by digestion with Alw44I/EcoRI and by sequencing over the cloning junctions (SYN04455:151-153)

Sequences used include SEQ ID NO. 9 (coding sequence), SEQ ID NO. 10 (promoter) and SEQ ID NO. 11 (terminator). SEQ ID NO: 9 encodes the protein of SEQ ID NO: 48.

c) Vector Construction for R-Gene Comprising SEQ ID NO: 12

Vector type: Binary Vector
Functional Description A binary vector for soybean transformation with glyphosate (EPSPS) selection harboring a soy rust resistance candidate gene from G. tomentella PI583970 that encodes a protein containing coiled-coiled (CC), nucleotide-binding site (NBS), and leucine rich repeat (LRR) domains expressed with native G. tomentella promoter and terminator (genomic DNA). The gene is syntenic to Glyma.05G165600 (Soy_william82_v2).

Sequences used include SEQ ID NO. 12 (coding sequence), SEQ ID NO. 13 (promoter) and SEQ ID NO. 14 (terminator). SEQ ID NO. 12 encodes the protein of SEQ ID NO: 42.

d) Vector Construction for R-Gene Comprising SEQ ID NO: 15

Vector type: Binary Vector
Construct Size (bp): 14,706
Functional description: Binary vector for soybean transformation with glyphosate selection (EPSPS), harboring a soy rust resistance candidate gene from Glycine tomentella (PI583970), cGtoRG13-01, encoding a protein containing coiled-coiled (CC), nucleotide-binding site (NBS), and leucine rich repeat (LRR) domains and driven by a soybean GmUbi promoter and Arabidopsis terminator plus a soybean kozak. The candidate gene is syntenic to Glyma.05G165600 (Soy_william82_v2).

Cloning methods: Site mutagenized U3962BF220-1 (prGmUBI1) so that the promoter fragment can be cut out using SanDI and BamHI (U1466CH300_6 by Genscript). Synthesized cGtoRG13 as a BamHI-SacI fragment (G519921, U1466CH300_6 by Genscript), cut out the fragment. Three way ligation into 23899 between SanDI and SacI sites to get VC21449 New (SYN03277: 183). Verified the construct by digestion using SalI and ApaLI as well as by HincII alone, followed by sequencing (SYN03277:184-185).

Sequences used include SEQ ID NO. 15 (coding sequence), SEQ ID NO. 16 (prGmUbi1-01 Native Ubiquitin 1 promoter from soybean; Accession D16248.1) and SEQ ID NO. 8 (Terminator tAtUBQ3-02 A at 328 bp from tAtUbq3-01 (Arabidopsis Ubq3 3'-UTR). SEQ ID NO: 15 encodes the protein of SEQ ID NO: 43.

e) Vector Construction for R-Gene Comprising SEQ ID NO: 18

Vector type: Binary Vector
Functional Description A binary vector for soybean transformation with glyphosate (EPSPS) selection harboring a soy rust resistance candidate gene from G. tomentella PI583970 that encodes a protein containing coiled-coiled (CC), nucleotide-binding site (NBS), and leucine rich repeat (LRR) domains expressed with Medicago truncatula promoter and Arabidopsis termintor plus a soybean kozak. The gene is syntenic to Glyma.05G165600 (Soy_william82_v2).

Cloning Instructions See VC21449 . . . replace prGmUbi1-01 with prMt51186-03 promoter. Ligate as SanDI/RsrII gene cassette to the SanDI site of 23614. Or if possible swap promoter directly from binary (SanDI/BamHI) vector made in VC21449.

Sequences used include SEQ ID NO. 18 (coding sequence), SEQ ID NO. 19 (Promoter prMt51186-03 The promoter from the Medicago truncatula gene identified by the GeneChip probe ID Mtr.51186.1.S1) and SEQ ID NO. 20 (Terminator Arabidopsis Ubiquitin UTR). SEQ ID NO: 18 encodes the protein of SEQ ID NO: 49.

f) Vector Construction for R-Gene Comprising SEQ ID NO: 21

Vector type: Binary Vector
Construct Size (bp): 16,801
Functional description: Binary vector for soybean transformation with Glyphosate selection (cmEPSPS), harboring a genomic fragment derived from Glycine tomentella (PI446958), gGtoRG11-01, to express a soy rust resistance candidate gene encoding a protein containing a coiled-coil, nucleotide binding site, and leucine-rich repeat domain (CC-NBS-LRR) The soy rust resistance gene is syntenic to Glyma.05G65600 (Soy_williams82_v2).

Cloning methods: Digested U8867CG170-1 with SanDI/SacI to obtain RG11-PartI fragment (4899 bp), Digested U8867CG170-2 with SacI/RsrII/Eam1105I to obtain RG11-PartII fragment (2609 bp), ligated these two fragments onto 20660 at SanDI site. The resulting construct VC21209 was confirmed by digestion with Alw44I/EcoRI/Bsp119I and by sequencing over the cloning junctions. (SYN04456:102-105). The resulting construct is 24160.

Sequences used include SEQ ID NO. 21 (coding sequence), SEQ ID NO. 22 (promoter) and SEQ ID NO. 23 (terminator). SEQ ID NO: 21 encodes the protein of SEQ ID NO: 44.

a) Vector Construction for R-Gene Comprising SEQ ID NO: 24

Vector type: Binary Vector
Functional Description Binary vector for soybean transformation to express the soy rust resistance candidate gene, cGtoRG11Ver221F, which encodes a protein containing a coiled-coil, nucleotide binding site, and leucine-rich repeat domain (CC-NBS-LRR). This gene is syntenic to Glyma.05G65600 (Soy_williams82_v2) and is derived from Glycine tomentella (PI446958) contig 221F allele, gGtoRG11-01. Expression is driven by the soybean Ubi1 promoter and *Arabidopsis* Ubq3 terminator. Vector utilizes Glyphosate selection (cmEPSPS).

Cloning Instructions Digest synthetic coding sequence (remove internal SacI site) with BamHI/SacI and ligate to the BamHI/SacI site of binary vector 24171 to replace the current CNL gene.

Note: promoter and terminator are the same as construct 24171

Sequences used include SEQ ID NO. 24 (coding sequence), SEQ ID NO. 25 (promoter) and SEQ ID NO. 26 (terminator). SEQ ID NO: 24 encodes the protein of SEQ ID NO: 45.

h) Vector Construction for R-Gene Comprising SEQ ID NO: 27

Vector type: Binary Vector

Allelic to CNL found in construct 24160. Identified by High Fidelity PCR amplification from PI446958 genomic DNA. Notebook Ref. SY04474:53

```
Forward Primer:
GGATTATGTTTATATTCGAGTACATGCTATTGC

Reverse Primer:
GGGATTCAAAGGCATCTTAGATTAGTCAAACATCC
```

Melting Temp: 98° C.
Annealing Temp: 58° C.
Elongation Temp: 72° C.
35 Cycles

PCR product was purified by agarose gel electrophoresis then sub-cloned into TOPO clone (PCR Blunt) vectors. Individual *E. coli* colonies were isolated on Kanamycin-LB selection media. Plasmid preps were prepared and the inserts sequenced.

Functional Description Binary vector for soybean transformation to express a soy rust resistance candidate gene, cGtoRG11Ver1F, which encodes a protein containing a coiled-coil, nucleotide binding site, and leucine-rich repeat domain (CC-NBS-LRR). This gene is syntenic to Glyma.05G65600 (Soy_williams82_v2) and is derived from *Glycine tomentella* (PI446958) contig 1F allele, similar to that of gGtoRG11-01. Expression is driven by the soybean Ubi1 promoter and *Arabidopsis* Ubq3 terminator. Vector utilizes Glyphosate selection (cmEPSPS).

Sequences used include SEQ ID NO. 27 (coding sequence), SEQ ID NO. 28 (promoter) and SEQ ID NO. 29 (terminator). SEQ ID NO: 27 encodes the protein of SEQ ID NO: 46.

i) Vector Construction for R-Gene Comprising SEQ ID NO: 30

Vector type: Binary Vector

Functional description: A binary vector for soybean transformation with ALS selection, haboring a candidate soy rust resistance gene encoding a protein containing a Toll-interleukin-like receptor (TIR), nucleotide binding site (NBS), leucine-rich repeat (LRR), WKRY domains syntenic to Glyma.05G165800 (Soy_william82_v2).

Cloning methods: GenScript synthesized RG5 as four fragments RG5-PartI, -PartII, -PartIII and -PartIV [U9490BJ270-5 (23955), U9490BJ270-6 (23956), U9490BJ270-7 (23957), and U9490BJ270-8 (23958)]. The first 3 fragments were cloned into the bridge vector 21177 as SanDI+Kpn2I respectively to obtain the intermediate 21177-PartI+II+III. Then the PartI+II+III (SanDI/Kpn2I) from this intermediate vector and PartIV (Kpn2I/RsrII) were all cloned into 22296 at once through three way ligation at SanDI site of 22296. The positive clone was confirmed by digestion with NcoI/HindIII and by sequencing over the cloning junctions (SYN04455:65-78).

Sequences used include SEQ ID NO. 30 (coding sequence), SEQ ID NO. 31 (promoter) and SEQ ID NO. 32 (terminator). SEQ ID NO: 30 encodes the protein of SEQ ID NO: 50.

Example 7 Validation of R-Genes Against ASR

Validation of Molecular Assay Using Fungal b-Tubulin's Transcripts as Measurement of Resistance In our phenotyping work, we have used both symptom evaluation and molecular assays for rust resistance or susceptibility ratings. The symptom evaluation is a modified version of a rust rating scale from Burdon and Speer, T A G, 1984. The molecular assay is based on a fungal housekeeping gene, b-tubulin, identified by a Syngenta scientist, the probe for b-tubulin targets a specific region in soy rust but not in other pathogens or plant species. Further we validated this molecular assay coupled with phenotypic symptomatic observations as shown in FIG. 9 and FIG. 1. FIG. 9, from left to right, top to bottom, depicts complete resistance (Rpp1 line), a few lesions without sporulation (Rpp5 lines), lots of lesions with little sporulations (Rpp6 line), many lesions with some Tan lesions plus sporulations (Rpp2 lines), to many Tan lesions with profuse sporulations (Rpp4, Rpp1b and Jack). Because the rust used in this example is virulent on Rpp4 and Rpp1b, these 2 lines show susceptibility as severe as the susceptible check, Jack.

Consistent with these observations, measurements taken using fungal b-tubulin transcripts shown in the graph of FIG. 1, from left to right, no detection of the transcripts (complete resistance, Rpp1 line), barely detectable level of transcripts (a few lesion without sporulation, Rpp5 and Rpp6 lines), low level of transcripts (lots of lesions with little sporulations, Rpp6 line), intermediate level of transcripts (many lesions with some Tan lesions/sporulations, Rpp2 lines), high level of transcripts (many Tan lesions with profuse sporulations, Rpp4, Rpp1b and Jack (CK) lines).

From these data sets, we have shown that a molecular assay using fungal b-tubulin or other housekeeping genes is as reliable and indicative as phenotypic symptomatic ratings, and provides higher resolution than phenotypic ratings based on symptoms.

Validation of Transient Foliar Gene Expression System Using Known Soy Rust R Gene A transient detached split-leaf assay was developed to validate rust resistance. This was accomplished by using a susceptible soybean, or its wild relatives, leaf and transiently expressing a GUS control vector on one side of the leaf and transiently expressing a vector containing an R-gene on the other side of the leaf (i.e. the leaf midrib being the divider, further the control and experimental vectors being similar except for the respective CDS (GUS or R-gene)). After 2-3 days of infiltration, leaves were sprayed with rust. At about 10-17 days, infiltrated leaves were selected and cut in half by the mid-vein divider. Left side (top view) of each leaf with only infiltrated area was cut out and filled in 1 well in a 96 well block, labeled as construct left-1. The right side (top view) of the leaf was cut out and filled in one well, the right half leaf filled the other, 8 pair of wells per construct. In each experiment, the right side of the leaves was infiltrated with construct containing GUS, while the left side was infiltrated with the constructs of interests. For GUS check, it means both sides of the leaf were infiltrated with constructs containing GUS. All of them were analyzed for fungal biomass measurement using quantitative polymerase chain reaction of fungal b-tubulin transcripts.

First we validated the system with GUS (in construct 17282) as negative check and CcRpp1 (soy rust R gene from *Cajanus cajan* in construct 23677). The CcRpp1 showed near 100% disease control in stable transgenic soybean when in homozygous state and protein level reach certain level (Kawashima et al., 2016 for soy rust resistance from pigeon pea). It is appropriate to be used as positive control for system validation. Both GUS and CcRpp1 constructs were co-infiltrated with construct 18515, a CFP construct for transformation efficiency measurement.

In quantitative reverse transcript polymerase chain reactions, three ways to process the data using transcripts of fungal b-tubulin and CFP. One could use CFP as transformation efficiency measurement. In this setting, the formula in FIG. 2 was used.

As shown in FIG. 3, construct containing CcRpp1 has significant less normalized fungal biomass accumulation compared to construct containing GUS at 95% confidence, while GUS check is not significant different from 1 which means amount of fungal biomass accumulated from two sides infiltrated with GUS are not statistically different. While the construct containing CcRpp1 infiltrated half leaves produced significantly less amount compared to the side infiltrated with construct containing GUS. This experiment was repeated once, and similar results obtained. In all experiments, a Syngenta elite line or *Glycine canescens* line was used. From this experiment, one with ordinary skill could argue that other soybean lines or close related legumes could be used as well.

We also tested the system without CFP transformation efficiency control. In this experiment, we compared constructs containing GUS, CcRpp1, and CNL from 583970 (construct 24230). 24230 is derived from genomic DNA amplied using primers designed from contigs 819F containing coiled-coiled nucleotide binding and leucine rich repeat (CNL). In this experiment, we tested if CFP transformation efficiency check can be skipped or not. Because there is not CFP in this experiment, the formula in FIG. 4 was used to process the transcript data for any given constructs.

As shown in FIG. 5, both CcRpp1 and 24230 (SEQ ID NO: 12) showed efficacy in rust resistance when compared to GUS negative check. But surprisingly, the 24230 appears more efficacious than CcRpp1. This may be due to the fact that CcRpp1 expression level is not sufficiently high to confer full resistance as it does in stable transgenics. However, it does reinforce the observation that the split leaf foliar expression is sufficient to detect resistance function.

We further tested other GUS construct as negative control. In this experiment, construct 21349 (GUS), and 24230 (CNL R gene from PI 583970, SEQ ID NO: 12) were used. As shown in FIG. 6, two sets of samples derived from 24230 are lower in fungal biomass than 21349. In this setting, we compared fungal b-tubulin from the side infiltrated with construct of interest directly to the other side infiltrated with construct containing GUS without normalization, except the value of transcript reads were processed by Log 2. Again the side infiltrated with construct 24230 showed significantly lower fungal biomass than the side infiltrated with construct containing GUS.

We also tested another construct, 23969 together with GUS check. 23969 contains another candidate gene in the chr 5 interval, encoding Toll inter-leukin nucleotide binding and leucine rich repeat protein with WRKY domain (TNLW). This resistance conferred by the gene in this construct is evident as indicated by significantly lower level of fungal biomass than GUS negative check (FIG. 6).

Stable Transformation with ASR Candidate Gene Vectors

*Agrobacterium tumefaciens* strains containing individual binary vector with PAT, ALS or EPSPS selectable marker gene and one or more of the soybean rust resistance candidate genes was transformed into explants prepared from imbibed soybean seeds as prepared by method described here (Khan 2004, U.S. Patent Application Publication No. 20040034889). Soybean seeds were selected from Jack, Williams 82 or a Syngenta elite variety such as 06KG 218440. FIGS. 7 and 8 show the data for stable transformants at the T1 (SEQ ID NO: 21) and T0 stage (SEQ ID NO: 27).

From the above data set, we have a reason to believe that both genes in the interval, CNL and TNLW, confer resistance to soybean rust. It would be reasonable to stack them to examine the resistance conferred by both genes together, a stronger resistance could be expected.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

From the above data set, we have a reason to believe that both genes in the interval, CNL and TNLW, confer resistance to soybean rust. It would be reasonable to stack them to examine the resistance conferred by both genes together, a stronger resistance could be expected.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11492637B2). An electronic copy of the "Sequence Listing" will also be available from the USPTO upon request and payment of the fee set forth in 37 CFR 1.19(b)(3).

The invention claimed is:

1. A nucleic acid comprising a nucleotide sequence operably linked to a heterologous regulatory element, wherein the nucleotide sequence comprises an R-gene encoding a protein having at least 90% sequence identity to SEQ ID NO: 47, wherein expression of said R-gene in a soybean plant enhances resistance to Asian Soybean Rust (ASR) compared to a plant not expressing the R-gene.

2. The nucleic acid of claim 1, wherein said R-gene encodes a protein having at least 95% sequence identity to SEQ ID NO: 47.

3. The nucleic acid of claim 2, wherein said R-gene encodes a protein having the amino acid sequence of SEQ ID NO: 47.

4. The nucleic acid of claim 1, wherein said R-gene comprises a nucleotide sequence having at least 90% sequence identity to SEQ ID NO: 6.

5. The nucleic acid of claim 1, wherein said R-gene is operably linked to a promoter active in a plant.

6. The nucleic acid of claim 5, wherein said promoter comprises a sequence having at least 95% sequence identity to SEQ ID NO: 7.

7. The nucleic acid of claim 5, wherein said promoter comprises the sequence of SEQ ID NO: 7.

8. A vector comprising the nucleic acid of claim 1.

9. A transgenic cell comprising the nucleic acid of claim 1.

10. The transgenic cell of claim 9, wherein the transgenic cell is a transgenic plant cell.

11. A plant or a plant part having stably incorporated into its genome an expression cassette comprising a nucleotide sequence operably linked to a heterologous regulatory element active in said plant, the nucleotide sequence comprising an R-gene encoding a protein having at least 90% sequence identity to SEQ ID NO: 47, wherein expression of said R-gene in said plant or plant part enhances resistance to Asian Soybean Rust (ASR) of said plant or plant part compared to a control plant not expressing said R-gene.

12. The plant or plant part of claim 11, wherein said protein has at least 95% sequence identity to SEQ ID NO: 47.

13. The plant or plant part of claim 12, wherein said protein comprises SEQ ID NO: 47.

14. The plant or plant part of claim 11, wherein said heterologous regulatory element comprises a promoter active in said plant or plant part and having at least 95% sequence identity to SEQ ID NO: 7.

15. The plant or plant part of claim 14, wherein said expression cassette comprises the promoter set forth in SEQ ID NO: 7.

16. The plant of claim 15, wherein said plant is a soybean plant.

17. The plant or plant part of claim 11, wherein the plant is a dicot plant.

18. The plant or plant part of claim 11, wherein the plant is a soybean plant.

19. The plant or plant part of claim 11, wherein the plant is a monocot.

20. A seed from the plant of claim 11, wherein said seed has stably incorporated into its genome said expression cassette.

21. The seed of claim 20, wherein said seed is a soybean seed.

22. An elite soybean plant comprising a nucleic acid comprising an R-gene encoding a protein sequence having at least 90% sequence identity to SEQ ID NO: 47 operably linked to a heterologous regulatory element active in the soybean plant, wherein expression of said R-gene in said plant enhances resistance to Asian Soybean Rust (ASR) compared to a control plant not expressing said R-gene.

23. The elite soybean plant of claim 22, wherein said R-gene encoding protein sequence is set forth in SEQ ID NO: 47.

24. The elite soybean plant of claim 22, wherein said R-gene comprises a nucleotide sequence as set forth in SEQ ID NO: 6.

25. The elite soybean plant of claim 22, wherein said heterologous regulatory element is a promoter having a nucleotide sequence as set forth in SEQ ID NO: 7.

26. A seed from the elite soybean plant of claim 22, wherein said seed comprises the heterologous R-gene.

27. The elite soybean plant of claim 22, wherein said R-gene was introduced by a breeding process.

28. The elite soybean plant of claim 22, wherein said R-gene was derived from *Glycine tomentella* accession line PI441001.

29. The elite soybean plant of claim 22, wherein the soybean plant has increased resistance to any one of the following: soy cyst nematode, bacterial pustule, root knot nematode, frog eye leaf spot, phytopthora, brown stem rot, nematode, Asian Soybean Rust, smut, *Golovinomyces cichoracearum, Erysiphe cichoracearum, Blumeria graminis, Podosphaera xanthii, Sphaerotheca fuliginea, Pythium ultimum, Uncinula necator, Mycosphaerella pinodes, Magnaporthe grisea, Bipolaris oryzae, Magnaporthe grisea, Rhizoctonia solani, Phytophthora sojae, Schizaphis graminum, Bemisia tabaci, Rhopalosiphum maidis, Deroceras reticulatum, Diatraea saccharalis, Schizaphis graminum* and *Myzus persicae*.

30. A method of controlling Asian Soybean Rust (ASR) in a field comprising the step of planting in the field a soybean plant, a plant part or a seed having stably incorporated into its genome a nucleic acid comprising an R-gene encoding a protein sequence having at least 90% sequence identity to SEQ ID NO: 47 operably linked to a heterologous regulatory element active in the soybean plant, wherein expression of said R-gene in said plant enhances resistance to ASR compared to a control plant not expressing said R-gene.

31. A harvested product derived from the seed of claim 26, wherein the harvested product comprises the R-gene encoding the protein having at least 90% sequence identity to SEQ ID NO: 47.

32. A processed product derived from the harvested product according to claim 31, wherein the processed product is a flour, a meal, an oil, a starch, or a product derived from any of the foregoing, wherein the processed product comprises the R-gene encoding the protein having at least 90% sequence identity to SEQ ID NO: 47.

33. A method of producing a plant with increased resistance to rust and comprising an R-gene, the method comprising introducing into a plant a nucleic acid molecule comprising an R-gene encoding a protein sequence having at least 90% sequence identity to SEQ ID NO: 47 operably linked to a heterologous regulatory element active in the plant, wherein the R-gene is expressed in the plant, thereby producing a plant with increased resistance to rust.

34. The method according to claim 33, wherein the introducing step comprises transforming a plant cell with the nucleic acid molecule and regenerating a transgenic plant.

35. The nucleic acid of claim 1, wherein said R-gene encodes a protein having at least 91% sequence identity to SEQ ID NO: 47.

36. The nucleic acid of claim 1, wherein said R-gene encodes a protein having at least 92% sequence identity to SEQ ID NO: 47.

37. The nucleic acid of claim 1, wherein said R-gene encodes a protein having at least 93% sequence identity to SEQ ID NO: 47.

38. The nucleic acid of claim 1, wherein said R-gene encodes a protein having at least 94% sequence identity to SEQ ID NO: 47.

39. The plant or plant part of claim 16, wherein said soybean plant is *Glycine max*.

40. The method according to claim 33, wherein the introducing step comprises crossing a first plant comprising the nucleic acid molecule with a second plant not comprising the nucleic acid molecule.

* * * * *